United States Patent
Ippoliti et al.

(10) Patent No.: US 10,870,646 B2
(45) Date of Patent: Dec. 22, 2020

(54) **OXAZOLIDINONES AND PHARMACEUTICAL COMPOSITIONS THEREOF FOR TREATING BACTERIAL INFECTIONS, INCLUDING INFECTION OF *MYCOBACTERIUM TUBERCULOSIS***

(71) Applicants: University of St. Thomas, St. Paul, MN (US); The Johns Hopkins University, Baltimore, MD (US)

(72) Inventors: J. Thomas Ippoliti, Woodbury, MN (US); Gyanu Lamichhane, Towson, MD (US)

(73) Assignees: University of St. Thomas, St. Paul, MN (US); The John Hopkins University, Baltimore, MD (US)

(*) Notice: Subject to any disclaimer, the term of this patent is extended or adjusted under 35 U.S.C. 154(b) by 0 days.

(21) Appl. No.: 16/489,234

(22) PCT Filed: Feb. 26, 2018

(86) PCT No.: PCT/US2018/019681
§ 371 (c)(1),
(2) Date: Aug. 27, 2019

(87) PCT Pub. No.: WO2018/157043
PCT Pub. Date: Aug. 30, 2018

(65) Prior Publication Data
US 2020/0002321 A1    Jan. 2, 2020

Related U.S. Application Data

(60) Provisional application No. 62/463,908, filed on Feb. 27, 2017.

(51) Int. Cl.
*C07D 413/10* (2006.01)
*A61P 31/04* (2006.01)
*A61P 31/06* (2006.01)
*C07D 417/14* (2006.01)
*C07D 498/06* (2006.01)

(52) U.S. Cl.
CPC ............ *C07D 413/10* (2013.01); *A61P 31/04* (2018.01); *A61P 31/06* (2018.01); *C07D 417/14* (2013.01); *C07D 498/06* (2013.01)

(58) Field of Classification Search
CPC .. C07D 413/04; C07D 413/14; C07D 491/06; C07D 413/10; C07D 417/14; C07D 498/06; A61P 31/04; A61P 31/06
See application file for complete search history.

(56) References Cited

U.S. PATENT DOCUMENTS

2002/0068720 A1* 6/2002 Sims .................. A61K 47/12
                                                      514/58

OTHER PUBLICATIONS

A. Kaushik et al., 26 Bioorganic & Medicinal Chemistry Letters, 3572-3576 (2016) (Year: 2016).*
D.C. Ebner et al., 16 Bioorganic & Medicinal Chemistry Letters, 2651-2656 (2008) (Year: 2008).*
Balasubramanian et al. "Bactericidal activity and mechanism of action of AZD5847, a novel oxazolidinone for treatment of tuberculosis," *Antimicrobial Agents and Chemotherapy*, 58 (2014) 495-502.
Barbachyn and Ford "Oxazolidinone structure-activity relationships leading to linezolid," *Angew Chem Int Ed Engl* 2003, 42(18):2010-2023.
Boucher. H.W. et al, Bad bugs, no drugs: no ESKAPE! An update from the Infectious Diseases Society of America, *Clinical infectious diseases*: an official publication of the Infectious Diseases Society of America, 48 (2009) 1-12.
Choy et al. "Development of a Synthesis for a Long-Term Oxazolidinone Antibacterial," *Org Process Res Dev* 2008, 12(5):884-887.
Desmond, "Susceptibility Testing of Mycobacteria, Nocardiae and Other Aerobic Actinomycetes," *Clinical Laboratory Standard Institute*, M24-A2 (2011).
Douros et al. "Drug-drug interactions and safety of linezolid, tedizolid, and other oxazolidinones," *Expert opinion on drug metabolism & toxicology*, 11 (2015) 1849-1859.
Due-Hansen et al. "A protocol for amide bond formation with electron deficient amines and sterically hindered substrates," *Organic & Biomolecular Chem* 2016, 14(2):430-433.
Fortun et al. "Linezolid for the treatment of multidrug-resistant tuberculosis," *J. Antimicrobial Chemotherapy*, 56 (2005) 180-185.
Gavan and Town, "A microdilution method for antibiotic susceptibility testing: an evaluation," *Amer. J. Clin. Path*, 53 (1970) 880-885.
"Protective Groups in Organic Synthesis," Theodora W. Greene (John Wiley & Sons, Inc., New York, 1991, ISBN 0-471-62301-6) (Book—Copy Not Provided).
"Greene's Protective Groups in Organic Synthesis," ISBN-13: 978-1118057483, ©2014, John Wiley & Sons, Inc. (5th Edition) (Book—Copy Not Provided).

(Continued)

*Primary Examiner* — Deepak R Rao
(74) *Attorney, Agent, or Firm* — Joseph T. Leone, Esq.; DeWitt LLP

(57) ABSTRACT

Disclosed are oxazolidinone compounds of Formula I: (I) salts thereof, antibacterial pharmaceutical compositions containing them, and use of the compounds to inhibit bacterial growth in mammals, including humans.

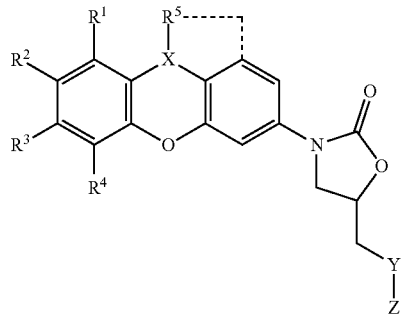

8 Claims, No Drawings

(56) References Cited

OTHER PUBLICATIONS

Hillemann et al. "In vitro-selected linezolid-resistant *Mycobacterium tuberculosis* mutants," *Antimicrobial Agents and Chemotherapy*, (2008) 800-801.
Hsieh et al. "Synergy assessed by checkerboard. A critical analysis," *Diagnostic Microbiology and Infectious Disease*, 16 (1993) 343-349.
Kaushik et al. "Carbapenems and Rifampicin Exhibit Synergy Against *Mycobacterium tuberculosis* and *Mycobacterium abscessus*," *Antimicrobial Agents and Chemotherapy*, (Oct. 2015) 59(10): 6561-6567.
Kaushik et al. "An evolved oxazolidinone with selective potency against *Mycobacterium tuberculosis* and gram positive bacteria," *Bioorg. & Med. Chem. Lett.* 2016, 26(15):3572-3576.
Kloss et al. "Resistance mutations in 23 S rRNA identify the site of action of the protein synthesis inhibitor linezolid in the ribosomal peptidyl transferase center," *J. Mol. Biol*, 294 (1999) 93-101.
Kocienski, Philip J. "Protecting Groups," (Georg Thieme Verlag Stuttgart, New York, 1994 (Book—Copy Not Provided).
Orlandi et al. "Metal-Free Reduction of Aromatic and Aliphatic Nitro Compounds to Amines: A HSiCl3-Mediated Reaction of Wide General Applicability," *Org. Lett* 2015, 17(16):3941-3943.
Perrault et al. "The Synthesis of N-Aryl-5(S)-aminomethyl-2-oxazolidinone Antibacterials and Derivatives in One Step from Aryl Carbamates," *Process Research & Development* 2003, 7:533-546.
Rhomberg and Jones, "Antimicrobial spectrum of activity for meropenem and nine broad spectrum antimicrobials: report from the Mystic Program (2002) in North America," *Diagnostic Microbiology and Infectious Disease*, 47 (2003) 365-372.
Rodriguez et al. "In vitro activity of moxifloxacin, levofloxacin, gatifloxacin and linezolid against *Mycobacterium tuberculosis,*" *Intl J. Antimicrobial Agents*, 20 (2002) 464-467.
Rosenthal, et al. "Dose-ranging comparison of rifampin and rifapentine in two pathologically distinct murine models of tuberculosis," *Antimicrobial Agents and Chemotherapy*, 56 (2012) 4331-4340.
Saager et al. "Molecular characterisation of linezolid resistance in two vancomycin-resistant (VanB) *Enterococcus faecium* isolates using pyrosequencing," *Eur. J. Clin Microbiol. & Inf. Diseases*: official publiccation of the European Society of Clinical Microbiology, 27 (2008) 873-878.
Schaus et al. "Dynamic Kinetic Resolution of Epichlorohydrin via Enantioselective Catalytic Ring Opening with $TMSN_3$ . Practical Synthesis of Aryl Oxazolidinone Antibacterial Agents," *Tetrahedron Lett* 1996, 37:7937.
Schumacher et al. "Intracellular accumulation of linezolid in *Escherichia coli, Citrobacter freundii* and *Enterobacter aerogenes*: role of enhanced efflux pump activity and inactivation," *J. of Antimicrob. Chemotherapy*, 59 (2007) 1261-1264.
Spellberg et al, "The epidemic of antibiotic-resistant infections: a call to action for the medical community from the Infectious Diseases Society of America," *Clinical infectious diseases*: an official publication of the Infectious Diseases Society of America, 46 (2008) 155-164.

P. Heinrich Stahl and Camille G. Wermuth (Eds.), "Pharmaceutical Salts: Properties, Selection, and Use, 2nd Edition," © 2011, Wiley-VCH (Zurich, Switzerland), ISBN-13: 978-3906390512 (Book—Copy Not Provided).
Tan et al. "Prospective evaluation of a matrix-assisted laser desorption ionization-time of flight mass spectrometry system in a hospital clinical microbiology laboratory for identification of bacteria and yeasts: a bench-by-bench study for assessing the impact on time to identification and cost-effectiveness," *J. of Clin.Microbiol.* 50 (2012) 3301-3308.
Tasneen et al. "Contribution of Oxazolidinones to the Efficacy of Novel Regimens Containing Bedaquiline and Pretomanid in a Mouse Model of Tuberculosis," *Antimicrobial Agents and Chemotherapy* 2015, 60(1):270-277.
Villar et al."Linezolid safety, tolerability and efficacy to treat multidrug- and extensively drug-resistant tuberculosis," *The European Respiratory Journal*, 38 (2011) 730-733.
Von Der Lippe et al. "Efficacy and safety of linezolid in multidrug resistant tuberculosis (MDR-TB)—a report of ten cases," *J. of Infection*, 52 (2006) 92-96.
Wallis et al. "Mycobactericidal activity of sutezolid (PNU100480) in sputum (EBA) and blood (WBA) of patients with pulmonary tuberculosis," *PloS One*, 9 (2014) e94462.
Walsh, C. "Antibiotics: Actions, Origins, Resistance," ASM Press, Washington DC, © 2003; ISBN 978-1555812546 (Book—Copy Not Provided).
("WHO: Global Tuberculosis Report," World Health Organization, Geneva, Switzerland; ISBN 978 92 4 156539 4, © 2016.
Williams et al. "Promising antituberculosis activity of the oxazolidinone PNU-100480 relative to that of linezolid in a murine model," *Antimicrobial Agents and Chemotherapy*, 53 (2009) 1314-1319.
Williams et al. "Addition of PNU-100480 to first-line drugs shortens the time needed to cure murine tuberculosis," *Amer. J. Respiratory and Critical Care Medicine*, 180 (2009) 371-376.
Zhang et al. "In vitro and in vivo activities of three oxazolidinones against nonreplicating *Mycobacterium tuberculosis,"* *Antimicrobial Agents and Chemotherapy*, 58 (2014) 3217-3223.
Zheng et al. "Siderophore-mediated cargo delivery to the cytoplasm of *Escherichia coli* and *Pseudomonas aeruginosa*: syntheses of monofunctionalized enterbactin scaffolds and evaluation of enterobactin-cargo conjugate uptake," *J. Amer. Chem. Soc.* 2012, 134(44):18388-18400.
Zhu et al. "A Two-Step, One-Pot, and Multigram-Scale Synthesis of N-Difluoromethylthiophthalimide," *Organic Process Research& Development* 2017, 21(9):1383-1387.
Zurenko et al. "In vitro activities of U-100592 and U-100766, novel oxazolidinone antibacterial agents," *Antimicrobial Agents and Chemotherapy*, 40 (1996) 839-845.
Ebner et al., 2008, Synthesis of novel oxazolidinone antimicrobial agents, Bioorganic & Medicinal Chemistry, 16:2651-2656.
Pandit et al., 2011, Current Updates on Oxazolidinone and Its Significance, International Journal of Medicinal Chemistry, vol. 2012, Article ID 159285, 24 pages.
Sridhar et al., 2015, Antibacterial activity of phenoxazine derivatives, Journal of Chemical and Pharmaceutical Research, 7(4):1074-1079, ISSN: 0975-7384.
PCT International Preliminary Report on Patentability/Written Opinion, dated Aug. 27, 2019, PCT/US2018/019681.

* cited by examiner

OXAZOLIDINONES AND PHARMACEUTICAL COMPOSITIONS THEREOF FOR TREATING BACTERIAL INFECTIONS, INCLUDING INFECTION OF MYCOBACTERIUM TUBERCULOSIS

CROSS-REFERENCE TO RELATED APPLICATIONS

Priority is hereby claimed to provisional application Ser. No. 62/463,908, filed Feb. 27, 2017, which is incorporated herein by reference.

BACKGROUND

In 2008, the Infectious Diseases Society of America (IDSA) made the following ominous declaration: "The ongoing explosion of antibiotic-resistant infections continues to plague global and US health care." Meanwhile, an equally alarming decline has occurred in the research and development of antibacterials to deal with the threat. (Spellberg et al, "The epidemic of antibiotic-resistant infections: a call to action for the medical community from the Infectious Diseases Society of America," Clinical infectious diseases: an official publication of the Infectious Diseases Society of America, 46 (2008) 155-164.) In 2009, IDSA sounded another alarm by stating "we remain concerned that the infrastructure for discovering and developing new antibacterials continues to stagnate, thereby risking the future pipeline." (H. W. Boucher, G. H. Talbot, J. S. Bradley, J. E. Edwards, D. Gilbert, L. B. Rice, M. Scheld, B. Spellberg, J. Bartlett, Bad bugs, no drugs: no ESKAPE! An update from the Infectious Diseases Society of America, Clinical infectious diseases: an official publication of the Infectious Diseases Society of America, 48 (2009) 1-12.) Of major concern are the community- and health care-associated infections with bacterial pathogens *Enterococcus faecium, Staphylococcus aureus, Klebsiella pneumoniae, Acinetobacter baumannii, Pseudomonas aeruginosa*, and *Enterobacter* species (commonly abbreviated as ESKAPE) that are increasingly becoming resistant to drugs available to treat them.

Additionally, the need for new anti-tuberculosis drugs cannot be overstated considering the emergence of drug-resistant strains and co-infections due to HIV/AIDS. In 2016, the World Health Organization declared tuberculosis (TB) as the leading cause of death due to infectious disease, even surpassing HIV/AIDS and malaria. ("WHO: Global Tuberculosis Report," World Health Organization, Geneva, Switzerland; ISBN 978 92 4 156539 4, © 2016.) Treating drug-resistant TB, for example, requires daily intake of drugs for at least one year. Many frontline antibiotics cannot be administered over such a long time frame as that results in significant toxicity. The toxicity of linezolid, a oxazolidinone antibiotic was identified in the course of such long-term dosing schedules. Thus, there is a long-felt and unmet need for effective antibacterial compounds that have less toxicity than current treatments and thus can be used to treat patients with drug-resistant TB.

SUMMARY OF THE INVENTION

Disclosed herein are oxazolidinone compounds of Formula I:

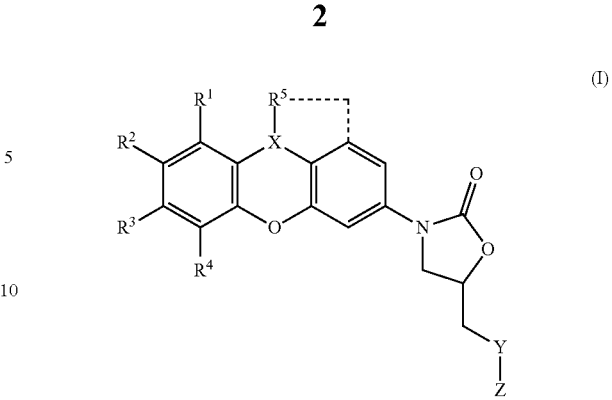

wherein:

X is selected from the group consisting of —N— and —O—;

when X is —O—, $R^5$ and the dotted bonds are absent;

when X is —N—, $R^5$ is selected from the group consisting of hydrogen, halogen, amino, $C_1$-$C_6$-alkyl, hydroxyl-substituted-$C_1$-$C_6$-alkyl, halo-substituted-$C_1$-$C_6$-alkyl, amino-substituted-$C_1$-$C_6$-alkyl, —C(=O)—$C_1$-$C_6$-alkyl-(O—$CH_2$—$CH_2)_{1-16}$—O—$C_1$-$C_6$-alkyl, —C(=O)—OR, —C(=O)R, —$C_1$-$C_6$-alkyl(=O)R, and —C(=O)—NRR, wherein each R is independently hydrogen or $C_1$-$C_6$-alkyl, unsubstituted or substituted with one or more hydroxyl or halo, or $R^5$ is —(C=O)— with X, $R^5$, the dashed bonds, and the carbons to which they are attached defining a 5-membered lactam ring;

Y is selected from the group consisting of —N(H)— and —O—;

Z is selected from the group consisting of H, —OH, —C(=O)—OH, —C(=O)—O—$C_1$-$C_6$-alkyl, —C(=O)-amino acid (C-linked or N-linked), —C(=O)-polypeptide having from two (2) to fifty (50) residues, an azole (as defined below), —C(=O)R, —$C_1$-$C_6$-alkyl(=O)R, and —C(=O)—NRR, wherein each R is independently hydrogen or $C_1$-$C_6$-alkyl, unsubstituted or substituted with one or more hydroxyl or halo;

$R^1$, $R^2$, $R^3$, and $R^4$ are independently selected from the group consisting of hydrogen, halogen, amino, $C_1$-$C_6$-alkyl, hydroxyl-substituted-$C_1$-$C_6$-alkyl, halo-substituted-$C_1$-$C_6$-alkyl, amino-substituted-$C_1$-$C_6$-alkyl, —C(=O)H, —C(=O)—OH, —C(=O)—O—$C_1$-$C_6$-alkyl, -aryl, -heteroaryl, -heterocyclyl, —$C_1$-$C_6$-alkyl-aryl, —$C_1$-$C_6$-alkyl-heteroaryl, —$C_1$-$C_6$-alkyl-heterocyclyl, —$C_1$-$C_6$-alkyl-amino-$SCF_2R$, —C(=O)R, —$C_1$-$C_6$-alkyl(=O)R, and —C(=O)—NRR, wherein each R is independently hydrogen or $C_1$-$C_6$-alkyl unsubstituted or substituted with one or more hydroxyl or halo, -linker-polypeptide (C-linked or N-linked) having from two (2) to fifty (50) residues, and -linker-siderophore;

provided that not all of $R^1$, $R^2$, $R^3$, and $R^4$ are simultaneously hydrogen; and salts thereof In certain versions of the compounds, Z is 3-isoxazole, 4-isoxazole, or 5-isoxazole. In other versions, it is preferred that $R^1$, $R^3$, and $R^4$ are hydrogen. When $R^1$, $R^3$, and $R^4$ are hydrogen, $R^2$ in the preferred compounds is selected from the group consisting of is halogen, amino, $C_1$-$C_6$-alkyl, hydroxyl-substituted-$C_1$-$C_6$-alkyl, halo-substituted-$C_1$-$C_6$-alkyl, amino-substituted-$C_1$-$C_6$-alkyl, —C(=O)—OH, —C(=O)—O—$C_1$-$C_6$-alkyl, -aryl, -heteroaryl, -heterocyclyl, —$C_1$-$C_6$-alkyl-aryl, —$C_1$-$C_6$-alkyl-heteroaryl, —$C_1$-

$C_6$-alkyl-heterocyclyl, —$C_1$-$C_6$-alkyl-amino-$SCF_2R$, —C(=O)R, —$C_1$-$C_6$-alkyl(=O)R, and —C(=O)—NRR, wherein each R is independently hydrogen or $C_1$-$C_6$-alkyl unsubstituted or substituted with one or more hydroxyl or halo, -linker-polypeptide having from two (2) to fifty (50) residues, and -linker-siderophore (as defined below).

In some versions of the compounds, $R^2$ is hydroxyl-substituted-$C_1$-$C_6$-alkyl, halo-substituted-$C_1$-$C_6$-alkyl, amino-substituted-$C_1$-$C_6$-alkyl, —C(=O)—OH, —C(=O)R, —$C_1$-$C_6$-alkyl(=O)R, and —C(=O)—NRR, wherein each R is independently hydrogen or $C_1$-$C_6$-alkyl unsubstituted or substituted with one or more hydroxyl or halo.

Thus, for example, when X is nitrogen, the compounds may appear as shown in Formula II:

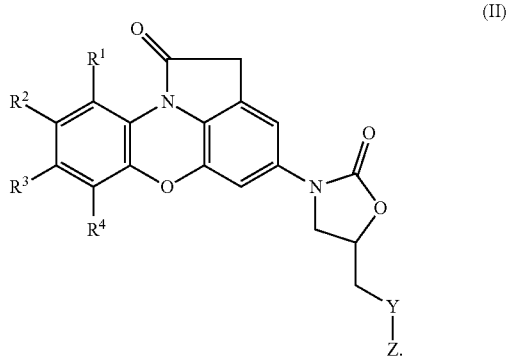

(II)

Also disclosed herein are pharmaceutical compositions comprising a bacterial growth-inhibiting amount of a compound of Formula I as disclosed herein, optionally in combination with a pharmaceutically suitable carrier.

Additionally disclosed herein is a method of inhibiting bacterial growth in a subject. The method comprises administering to the subject a bacterial growth-inhibiting amount of a compound of Formula I as disclosed herein. The subject may be a mammal, including humans.

DETAILED DESCRIPTION

Abbreviations and Definitions

The term "alkyl" refers to a branched or unbranched carbon chain having, for example, about 1-20 carbon atoms, and often 1-12, 1-10, 1-8, 1-6, or 1-4 carbons. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated in certain embodiments. As such, the recitation of an alkyl group optionally includes both alkenyl and alkynyl groups. The alkyl can be a monovalent hydrocarbon radical, as described and exemplified above, or it can be a divalent hydrocarbon radical (i.e., an alkylene).

The term "aryl", as used herein, refers to aromatic monocyclic or multicyclic, some of which may be fused together, hydrocarbon ring system consisting only of hydrogen and carbon and containing from 6 to 19 carbon atoms (represented as ($C_6$-$C_{19}$)aryl), preferably 6 to 10 carbon atoms (represented as ($C_6$-$C_{10}$)aryl), where the ring system may be partially or fully saturated. Aryl groups include, but are not limited to groups such as fluorenyl, phenyl and naphthyl. Unless stated otherwise specifically in the specification, the term "aryl" is meant to include aryl radicals optionally substituted by one or more substituents selected from ($C_1$-$C_{12}$)hydrocarbyl, —O—R", —O—CO—R", —CO—O—R", —NR'—R", —NR'—CO—R", —CO—NR'—R", —CO—R", —R—O—R", —R—O—CO—R", —R—CO—O—R", —R—NR'—R", —R—NR'—CO—R", —R—CO—NR'—R", —R—CO—R", —CN, halogen, or a combination thereof, wherein R' and R" are independently H or ($C_1$-$C_{12}$)hydrocarbyl, and R is ($C_1$-$C_{12}$)hydrocarbyl.

The term "heteroaryl", as used herein, refers to a 5- to 18-membered monocyclic- or bicyclic- or fused polycyclic-ring system which consists of carbon atoms and from one to five heteroatoms selected from the group consisting of nitrogen, oxygen and sulfur. Preferably heteroaryl is a 5- to 12- or 5- to 9-membered ring system. For purposes of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from ($C_1$-$C_{12}$)hydrocarbyl, —O—R", —O—CO—R", —CO—O—R", —NR'—R", —NR'—CO—R", —CO—NR'—R", —CO—R", —R—O—R", —R—O—CO—R", —R—CO—O—R", —R—NR'—R", —R—NR'—CO—R", —R—CO—NR'—R", —R—O—R", —R—CO—R", —CN, halogen, or a combination thereof, wherein R' and R" are independently H or ($C_1$-$C_{12}$)hydrocarbyl, and R is ($C_1$-$C_{12}$)hydrocarbyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

The term "cycloalkyl", as used herein, refers to a stable non-aromatic monocyclic or bicyclic hydrocarbon radical consisting solely of carbon and hydrogen atoms, having from three to fifteen carbon atoms, preferably having from three to twelve carbon atoms, ($C_3$-$C_{12}$)cycloalkyl, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from —O—R", —O—CO—R", —CO—O—R", —NR'—R", —NR'—CO—R", —CO—NR'—R", —CO—R", —CN, halogen, or a combination thereof, wherein R' and R" are independently H or ($C_1$-$C_{12}$)hydrocarbyl.

The terms "heterocyclyl" or "heterocycle", as used herein, refer to an optionally substituted, saturated or partially unsaturated, nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2, 3, or 4 heteroatoms independently selected from nitrogen atoms, oxygen atoms and sulfur atoms, wherein the nitrogen and sulfur heteroatoms may also optionally be oxidized. The heterocyclic group may be attached at a heteroatom or a carbon atom. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. The bicyclic and tricyclic heterocyclyl groups can be fused or spiro rings or ring groups. Preferably heterocyclyl is a 4- to 12-membered ring system. Also preferably heteocyclyl is a 4- to 9-membered ring system.

Exemplary monocyclic heterocyclic groups include oxetanyl, thiatanyl, azetidinyl, dihydrofuranyl, tetrahydrofuranyl, dihydrothiophenyl, tetrahydrothiophenyl, pyrrolidinyl, dihydropyrazolyl, tetrahydropyrazolyl, dihydropyridinyl, tetrahydropyridinyl, dihydrothiopyranyl, tetrahydrothipyranyl, pyranyl, dihydropyranyl, tetrahydropyranyl, thiopyranyl, dihydrothiopyranyl, tetrahydrothiopyranyl, ptperidinyl, piperazinyl, morphoiinyl, azepinyl, dihydroazepinyl, tetrahydroazepinyl, 2-oxopiperazinyl, 2-oxopiperidinyl, 2-oxopyrrolodinyl, 2-oxoazepinyl, oxepanyl, thiepanyl, dihyrothiepinyl, tetrahydrothiepinyl, dihydrooxepinyl, tetrahydrooxepinyl, 1,4-dioxanyl, 1,4-oxathianyl, morpholinyl, oxazolyl, oxazolidinyl, isoxazolinyi, isoxazolyl, 1,4-azathianyl, 1,4-oxathiepanyl, 1,4-oxaazepanyl, 1,4-dithiepanyl, 1,4-thieaxepanyl, 1,4-diazepanyl, tropanyl, 3,4-dihydro-2H-pyranyl, 5,6-dihydro-2H-pyranyl, thiazolidinyl, thiomorpholinyl, thiomorpholinyl sulfoxide, thiomorpholinyl sulfone, 1,3-dioxolane and tetrahydro-1,1-dioxothienyl, 1,1,4-trioxo-1,2,5-thiadiazolidin-2-yl, pyrazolinyl, and the like.

Exemplary bicyclic heterocyclic groups include but are not limited to, dihydroindolyl, quinuclidinyl, tetrahydroquinolinyl, decahydroquinolinyl, 2-oxa-6-azaspiro[3,3]heptan-6-yl, tetrahydroisoquinoiinyl, decahydroisoquinoiinyl, dihydroisoindolyl, indoiinyl, norboranyl, adamantanyl, and the like.

Unless stated otherwise specifically in the specification, the term "heterocyclyl" is meant to include heterocyclyl radicals as defined above which are optionally substituted by one or more substituents selected from —O—R", —O—O—R", —CO—O—R", —NR'—R", —NR'—CO—R", —CO—NR'—R", —CO—R", —CN, halogen, or a combination thereof, wherein R' and R" are independently H or ($C_1$-$C_{12}$)hydrocarbyl.

The term "direct bond", as used herein, means that the two entities linked by the "direct bond" are connected to each other directly. The direct bond may be a single bond or a double bond, for example.

"Azole(s)" are a class of five-membered, unsaturated heterocyclic compounds containing a nitrogen atom and at least one other non-carbon atom (specifically a nitrogen, sulfur, or oxygen heteroatom) as part of the ring. The terms "azole" explicitly includes, but is not limited to:

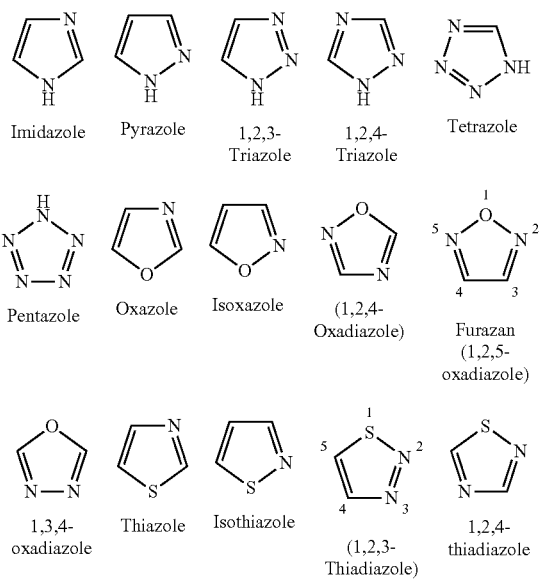

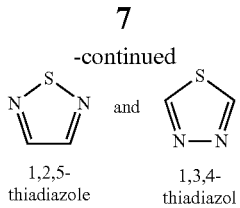

1,2,5-thiadiazole  and  1,3,4-thiadiazol

"Benzodioxine," refers to 10H-phenoxazine:

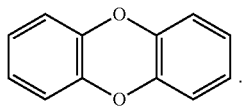 [SMILES: c1ccc2c(c1)Oc1ccccc1O2]

"Phenoxazine" refers to 10H-phenoxazine:

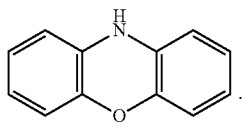 [SMILES: c1ccc2c(c1)Nc1ccccc1O2]

"Oxazolidinone" refers generally to 2-oxazolidinone:

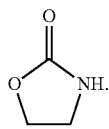

"Oxazolidinones" (plural) is used generically to refer to compounds disclosed herein that contain an oxazolidinone moiety linked via its nitrogen atom to a larger molecule.

The term "contacting" refers to the act of touching, making contact, or of bringing to immediate or close proximity, including at the molecular level, for example, to bring about a chemical reaction, or a physical change, e.g., in a solution or in a reaction mixture.

"C-linked" and "N-linked" when referring to an amino acid or a polypeptide, means that the amino acid or polypeptide moiety is attached to the remainder of the molecule via its carboxy terminus (C-linked) or its amino terminus (N-linked)

An "effective amount" refers to an amount of a chemical or reagent effective to facilitate a chemical reaction between two or more reaction components, and/or to bring about a recited effect. Thus, an "effective amount" generally means an amount that provides the desired effect.

The compounds disclosed herein may include one or more stereocenters, and thus exhibit stereoisomerism. The compounds disclosed herein include single enantiomers and/or diastereomers thereof, racemic mixtures thereof, and mixtures of enantiomers/diastereomers in any ratio of enantiomeric excess.

"Halo" and "halogen" mean chlorine, fluorine, bromine and iodine.

"Isoxazole" is an azole with an oxygen heteroatom next to the nitrogen heteroatom:

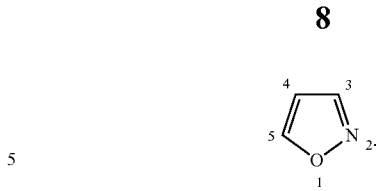

As used herein, a "linker" bridges two moieties in a molecule. A "linker" may be a divalent hydrocarbyl chain (e.g., $(C_1-C_{12})$alkylene, $(C_2-C_{12})$alkenylene), optionally substituted with a substituent group, or a linker may be a hydrocarbyl chain interspersed with other atoms, as represented by —$(CHR')_a$—$W_b$—$(CHR')_c$—$V_d$—$(CHR')_e$—, wherein W and V are independently —O—, —S—, or —NR—; R' is H or $(C_1-C_6)$alkyl; and a, b, c, d, and e are independently an integer from 0 to 10, preferably from 0 to 6, or preferably from 0 to 3, and the sum of a, b, c, d, and e is preferably an integer from 2 to 6. The optional substituent group may be —O—R", —O—CO—R", —NR'—R", —NR'—CO—R", —CO—NW—R", —CO—R", —CN, halogen, or a combination thereof, wherein R' and R" are independently H or $(C_1-C_6)$ hydrocarbyl.

"Pharmaceutically suitable salt" or "pharmaceutically acceptable salt" refers any acid or base addition salt whose counter-ions are non-toxic to the patient in pharmaceutical doses of the salts, so that the beneficial inhibitory effects inherent in the free base or free acid are not vitiated by side effects ascribable to the counter-ions. A host of pharmaceutically-suitable salts are well known in the art. For basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures. Pharmaceutically-suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates, quinates, and the like. Base addition salts include those derived from alkali or alkaline earth metal bases or conventional organic bases, such as triethylamine, pyridine, piperidine, morpholine, N-methylmorpholine, and the like. See, for example, P. Heinrich Stahl and Camille G. Wermuth (Eds.), "Pharmaceutical Salts: Properties, Selection, and Use, 2nd Edition," © 2011, Wiley-VCH (Zurich, Switzerland), ISBN-13: 978-3906390512.

A "protecting group" is any chemical moiety capable of selective addition to and removal from a reactive site to allow manipulation of a chemical entity at sites other than the reactive site. Many protecting groups are known in the art. A large number of protecting groups and corresponding chemical cleavage reactions are described in "Protective Groups in Organic Synthesis," Theodora W. Greene (John Wiley & Sons, Inc., New York, 1991, ISBN 0-471-62301-6) ("Greene", which is incorporated herein by reference). See also the 5th edition of this same work, published under the title "Greene's Protective Groups in Organic Synthesis," ISBN-13: 978-1118057483, ©2014, John Wiley & Sons, Inc. Greene describes many nitrogen protecting groups, for example, amide-forming groups. In particular, see Chapter 1, Protecting Groups: An Overview, Chapter 2, Hydroxyl Protecting Groups, Chapter 4, Carboxyl Protecting Groups, and Chapter 5, Carbonyl Protecting Groups. For additional information on protecting groups, see also Kocienski, Philip J. "Protecting Groups," (Georg Thieme Verlag Stuttgart, New York, 1994), which is incorporated herein by reference. Typical nitrogen protecting groups described in Greene include benzyl ethers, silyl ethers, esters including sulfonic acid esters, carbonates, sulfates, and sulfonates. For example, suitable nitrogen protecting groups include substituted methyl ethers; substituted ethyl ethers; p-chlorophenyl, p-methoxyphenyl, 2,4-dinitrophenyl, benzyl; substituted benzyl ethers (p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, diphenylmethyl, 5-dibenzosuberyl, triphenylmethyl, p-methoxyphenyl-diphenylmethyl, di(p-methoxyphenyl)phenylmethyl, tri(p-methoxyphenyl)methyl, 1,3-benzodithiolan-2-yl, benzisothiazolyl S,S-dioxido); silyl ethers (silyloxy groups) (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, t-butylmethoxy-phenylsilyl); esters (formate, benzoylformate, acetate, choroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), pivaloate, adamantoate, crotonate, 4-methoxycrotonate, benzoate, p-phenylbenzoate, 2,4,6-trimethylbenzoate(mesitoate)); carbonates (methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate); groups with assisted cleavage (2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, miscellaneous esters (2,6-dichloro-4-methylphenoxyacetate, 2,6-dichloro-4-(1,1,3,3 tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate (tigloate), o-(methoxycarbonyl)benzoate, p-poly-benzoate, a-naphthoate, nitrate, alkyl N,N,N',N'-tetramethyl-phosphorodiamidate, n-phenylcarbamate, borate, 2,4-dinitrophenylsulfenate); or sulfonates (methanesulfonate(mesylate), benzenesulfonate, benzylsulfonate, tosylate, or triflate).

The more common of the amine-protecting groups have trivial abbreviations that are widely used in the literature and include: carbobenzyloxy (Cbz) group (removed by hydrogenolysis), p-methoxybenzyl carbonyl (Moz or MeOZ) group (removed by hydrogenolysis), tert-butyloxycarbonyl (BOC) group (common in solid phase peptide synthesis; removed by concentrated strong acid (such as HCl or CF3COOH), or by heating to >80° C., 9-fluorenylmethyloxycarbonyl (FMOC) group (also common in solid phase peptide synthesis; removed by base, such as piperidine), acetyl (Ac) group (removed by treatment with a base), benzoyl (Bz) group (removed by treatment with a base), benzyl (Bn) group (removed by hydrogenolysis), carbamate group (removed by acid and mild heating), p-methoxybenzyl (PMB) (removed by hydrogenolysis), 3,4-dimethoxybenzyl (DMPM) (removed by hydrogenolysis), p-methoxyphenyl (PMP) group (removed by ammonium cerium(IV) nitrate (CAN)), tosyl (Ts) group (removed by concentrated acid and strong reducing agents), sulfonamide groups (Nosyl & Nps; removed by samarium iodide, tributyltin hydride).

The term "siderophore" refers broadly to any chemical moiety that is a high-affinity chelator of $Fe^{3+}$. This includes catecholates, hydroxamates, and carboxylates. For example, hydroxamate siderophores include (but are not limited to) ferrichrome, desferrioxamine B, desferrioxamine E, fusarinine C, ornibactin, and rhodotorulic acid. Catecholate siderophores include enterobactin, bacillibactin, and vibriobactin. Other siderophores include azotobactin, pyoverdine, and yersiniabactin.

The term "solvent" refers to any liquid that can dissolve a compound to form a solution. Solvents include water and various organic solvents, such as hydrocarbon solvents, for example, alkanes and aryl solvents, as well as halo-alkane solvents. Examples include hexanes, benzene, toluene, xylenes, chloroform, methylene chloride, dichloroethane, and alcoholic solvents such as methanol, ethanol, propanol, isopropanol, and linear or branched (sec or tert) butanol, and the like. Aprotic solvents that can be used in the method include, but are not limited to perfluorohexane, α,α,α-trifluorotoluene, pentane, hexane, cyclohexane, methylcyclohexane, decalin, dioxane, carbon tetrachloride, freon-11, benzene, toluene, triethyl amine, carbon disulfide, diisopropyl ether, diethyl ether, t-butyl methyl ether (MTBE), chloroform, ethyl acetate, 1,2-dimethoxyethane (glyme), 2-methoxyethyl ether (diglyme), tetrahydrofuran (THF), methylene chloride, pyridine, 2-butanone (MEK), acetone, hexamethylphosphoramide, N-methylpyrrolidinone (NMP), nitromethane, dimethylformamide (DMF), acetonitrile, sulfolane, dimethyl sulfoxide (DMSO), propylene carbonate, and the like.

The term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl(alkyl)amine, and cyano. Additionally, suitable substituent groups can be, e.g., —X, —R, —O—, —OR, —SR, —S—, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O—, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=OXO-)$_2$, —P(=O)(OH)$_2$, —C(=O)R, —C(=O)X, —C(S)R, —C(O)OR, —C(O)O—, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (═O) or thioxo (═S), or the like, then two hydrogen atoms on the substituted atom are replaced. In some embodiments, one or more of the substituents above are excluded from the group of potential values for substituents on the substituted group.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described herein, as well as any additional or optional ingredients, components, or limitations described herein or otherwise useful in synthetic organic chemistry.

The Novel Compounds, how to Make them, how to Use them:

To address potential solubility issues, a set of new oxazolidinones containing the same benzodioxin core as T145 (see below) was designed. This set of compounds is designated Y1-1 through Y1-6 and is shown in Scheme 1. These compounds contain functional groups that are good hydrogen bonders and should increase binding to the active site, as well as enhance water solubility. All of the new functional groups introduced are quite distinct, structurally, from the oxazolidinone ring.

Scheme 1. Novel oxazolidinone compounds Y1-1 through Y1-6

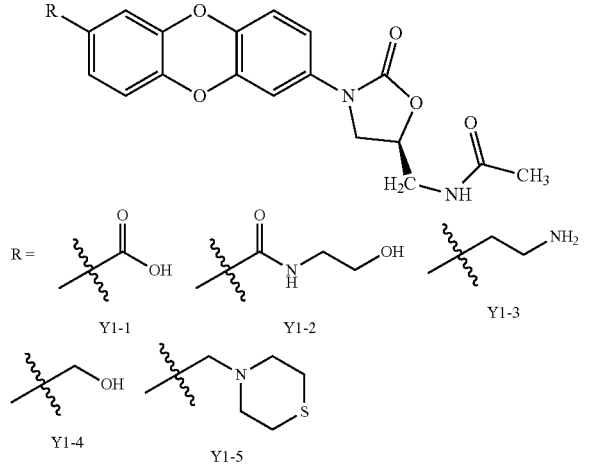

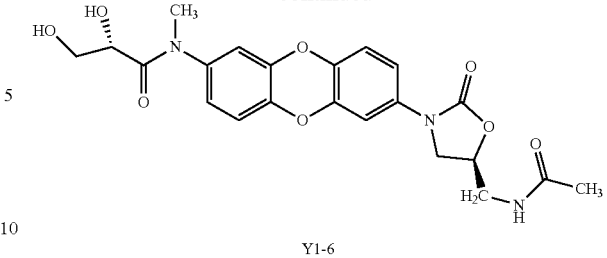

Y1-6

In another version of the compounds, a nitrogen atom is introduced in place of one of the oxygen atoms in the dibenzodioxin ring. It is postulated that the greater electron donating ability of the nitrogen in a phenoxazine ring will enhance the binding, and thus the antimicrobial effectiveness, of oxazolidinone antibiotics. The current inventors believe this is the first time a phenoxazine ring system has been modified to include an oxazolidinone moiety. These molecules, designated Y2-1 through Y2-6, are shown in Scheme 2.

Scheme 2. Novel oxazolidinone compounds Y2-1 through Y2-6

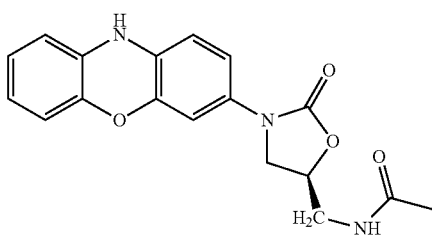

Y2-1

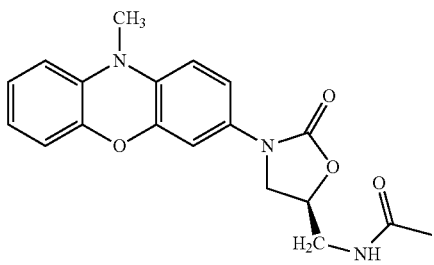

Y2-2

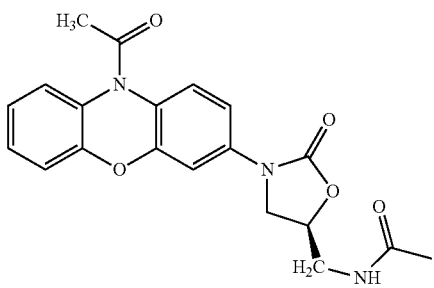

Y2-3

Y2-4

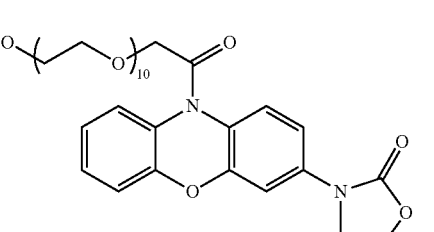

Y2-5
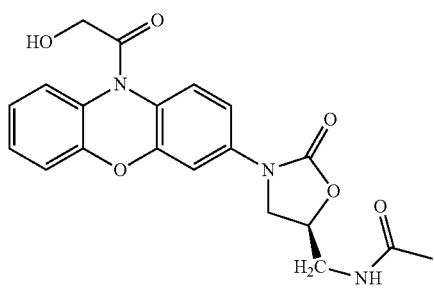

Y2-6
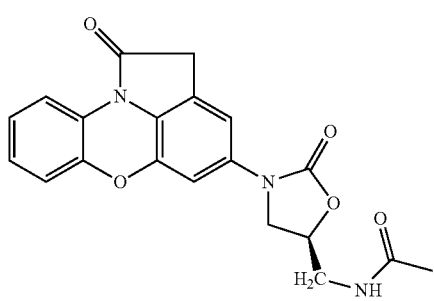

The inventors also postulate that halogen atoms, especially fluorine atom, will increase the ability of the dibenzodioxin ring to bind to the active site. It is also thought that incorporating siderophores and short peptide appendages will enhance the ability of these oxazolidinones to penetrate the cell wall. Substitution of fluorine for hydrogen has led to many active drug molecules. There are several positions in T145 that are suitable for halogen substitution. Because fluorine has minimal steric requirements and can influence pKa as well as metabolic stability it is commonly incorporated into biologically active molecules. Three examples of halogen-substituted molecules are shown in Scheme 3. Compound Y3-3 is especially interesting because this thiodifluoromethyl group has strong hydrogen-bonding properties.

Scheme 3. Halogenated Oxazolidinones Y3-1 through Y3-3.

Y3-1
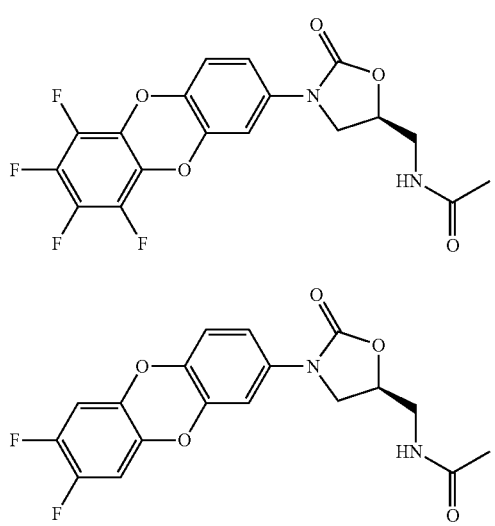

Y3-2
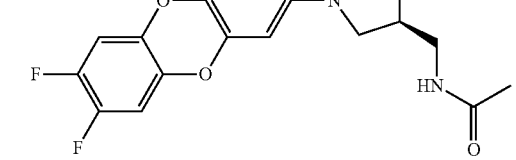

Y2-5
Y3-3
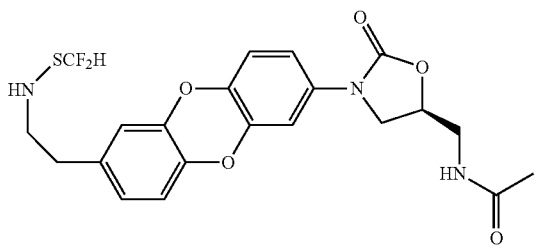

As noted above, one approach that has not been attempted in the oxazolidinone field is to add peptides (with D and/or L amino acids) or siderophores to tune the solubility and cell penetration of the oxazolidinone core. To address this deficiency compounds Y3-4, Y3-5 and Y3-6 as shown in Scheme 4 were designed.

Scheme 4. Oxazolidinones
incorporating tripeptides and Enterobactin siderophore.

Y3-4
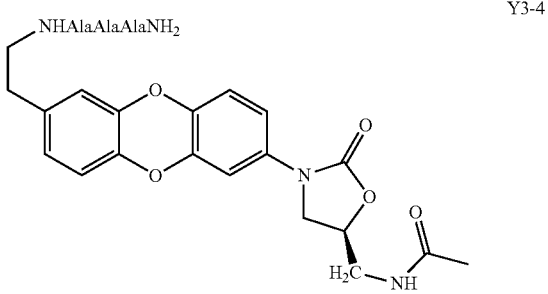

Y3-5
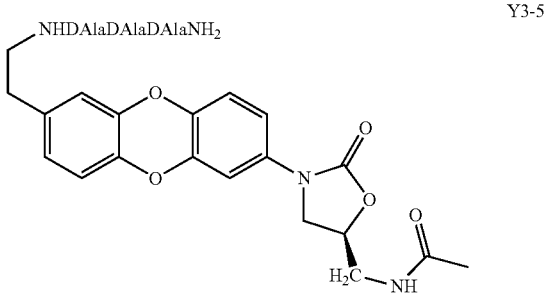

Y3-6
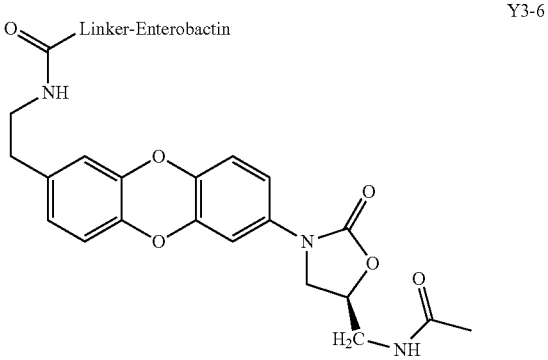

An important feature of any antibiotic is its ability to bind to the active site of the enzyme it is proposed to inhibit. The X-ray crystal structure of Linezolid bound to the 50S ribosomal subunit of *Haloarcula marismortui* (HMA) at a resolution of 2.7 Å clarified the binding mode and requirements for high affinity binding observed for this compound.

(Ippolito et al. "Crystal structure of the oxazolidinone antibiotic linezolid bound to the 50S ribosomal subunit," *J. of Med Chem.* 2008, 51(12):3353-3356.) Any new oxazolidinone designed should fit this active site. The cavity where the morpholine ring and F atom reside is quite large and this cavity can accommodate fairly large structures such as the oxazolidinone T145 (see below). Without being limited to any underlying mechanism, presumably, T145 fits this active site quite well based on its outstanding activity. The X-ray structure indicates that the morpholine ring does not appear to have significant interactions with the ribosome, which is consistent with the fact that many different functional groups can be substituted for the morpholine without a significant loss of activity. See Barbachyn and Ford "Oxazolidinone structure-activity relationships leading to linezolid," *Angew Chem Int Ed Engl* 2003, 42(18):2010-2023.

Synthesis of Compounds:

The synthetic schemes to make each of the compounds outlined above are shown in the following schemes.

Scheme 5 depicts the synthetic route to Y1-1 and Y1-2. The introduction of acidic protons into the structure dictates the use of protecting groups. Scheme 5 also illustrates an isomer issue that occurs in the first step. As indicated these isomers are separated by column chromatography. A number of suitable columns are available commercially, including a Biotage®-brand Ultra KP-SIL column (Biotage AB, Uppsala, Sweden). The ability to isolate either isomer provides the potential to make the single isomer versions of the oxazolidinones that utilize an unsymmetrical diol in the first step to make the dioxin ring.

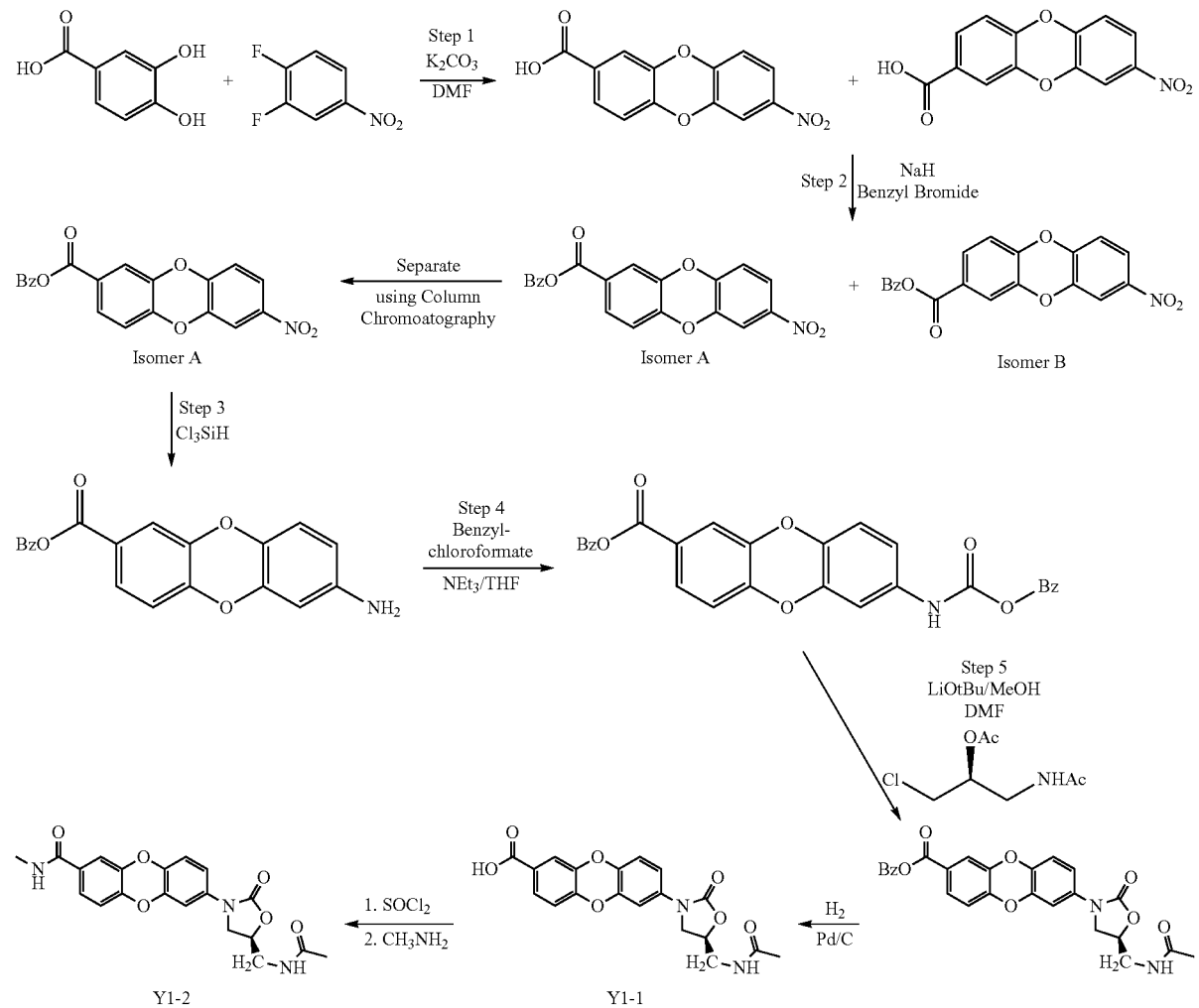

Scheme 5

In step 3, a selective reducing agent ($HSiCl_3$) is employed; in practice, we have found this to be an excellent way to reduce the nitro group in the presence of groups sensitive to the preferred hydrogenation route. Orlandi et al. "Metal-Free Reduction of Aromatic and Aliphatic Nitro Compounds to Amines: A $HSiCl_3$-Mediated Reaction of Wide General Applicability," *Org. Lett* 2015, 17(16):3941-3943. The oxazolidinone-forming step (step 5 in Scheme 5) is based on an efficient synthesis originally developed by Jacobsen and shown to be effective on large scale by Perrault. Jacobsen et al. "Dynamic Kinetic Resolution of Epichlorohydrin via Enantioselective Catalytic Ring Opening with TMSN3. Practical Synthesis of Aryl Oxazolidinone Antibacterial Agents," *Tetrahedron Lett* 1996, 37:7937; Perrault et al. "The Synthesis of N-Aryl-5(S)-aminomethyl-2-oxazolidinone Antibacterials and Derivatives in One Step from Aryl Carbamates," *Process Research & Development* 2003, 7:533-546. This route to form the oxazolidinone ring is highly flexible and used extensively to make the compounds disclosed herein. Hydrogenation reactions employed herein are extremely rapid and efficient utilizing an H-Cube Pro-brand flow hydrogenation reactor (ThalesNano Nanotechnology, Inc., Budapest, Hungary). Schemes 6, 7, and 8 below again utilize protecting groups to ensure the efficient formation of the oxazolidinone ring.

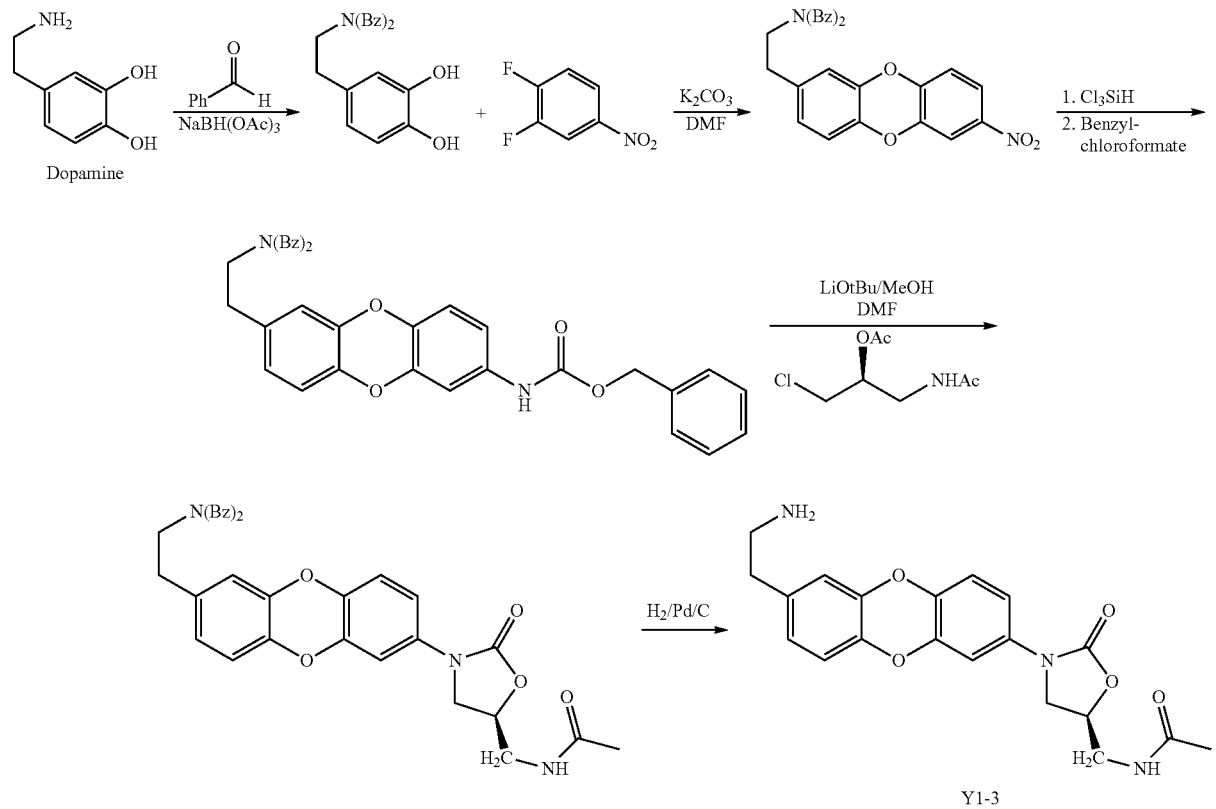

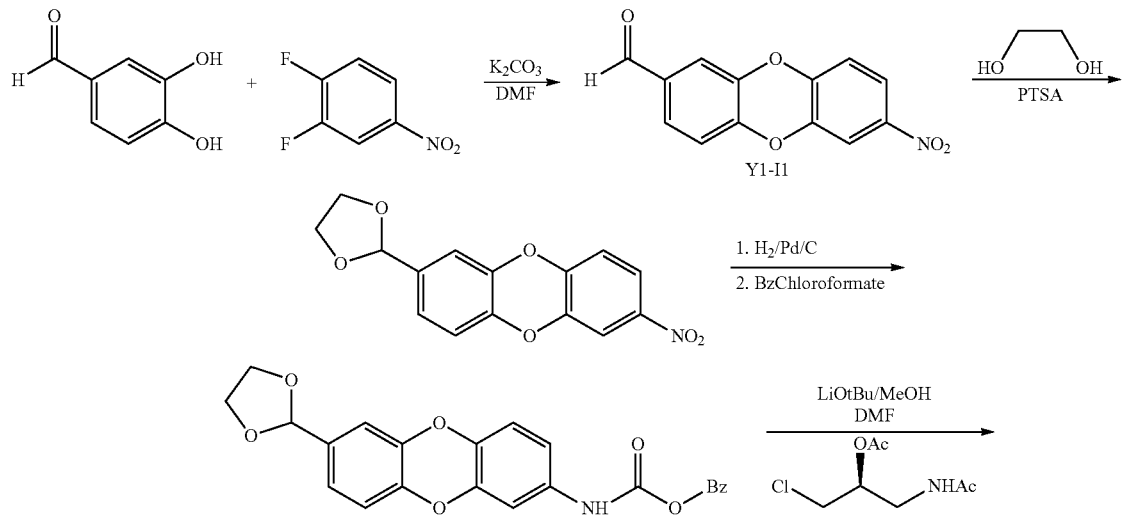

-continued
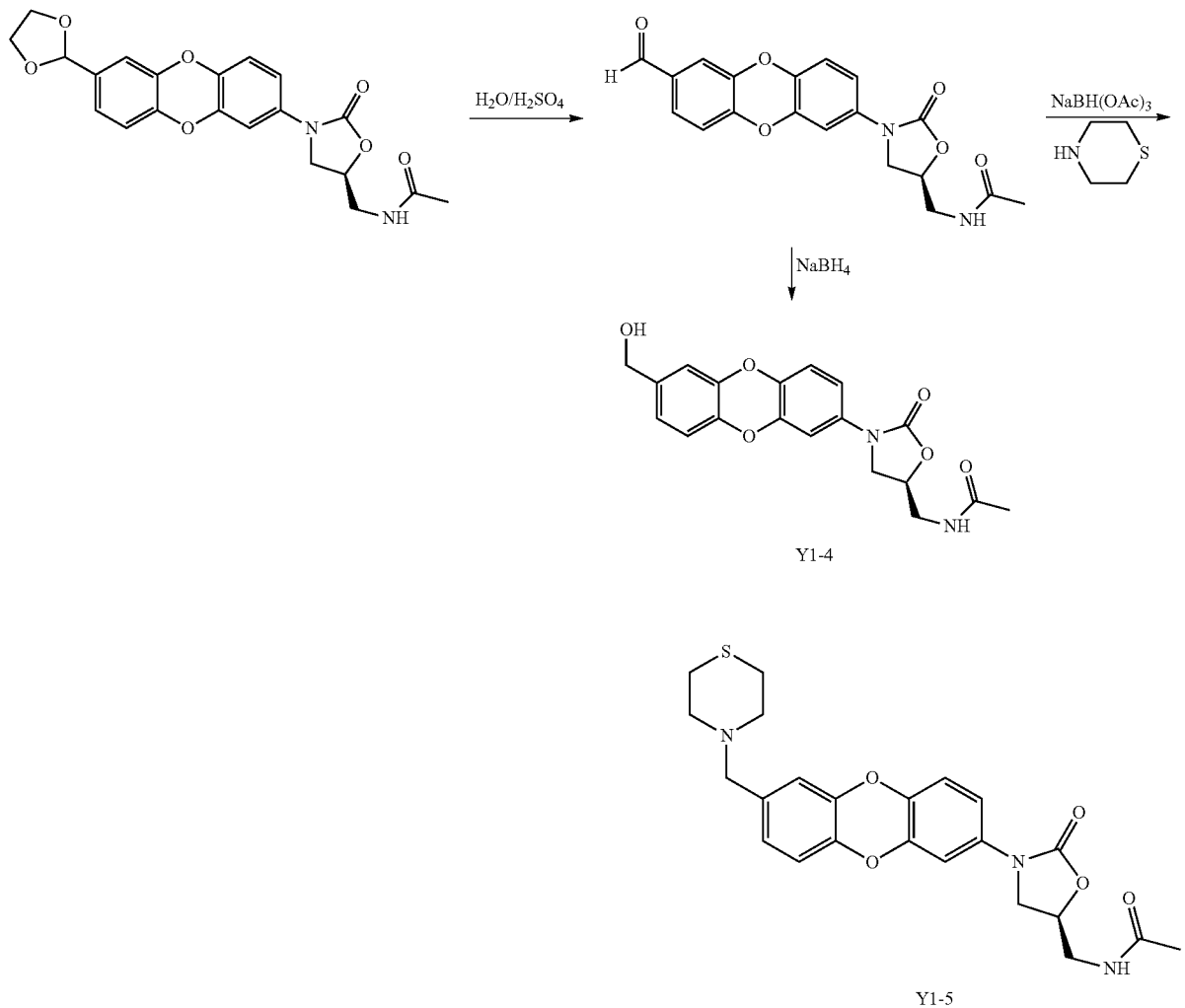
Y1-4
Y1-5
Scheme 8
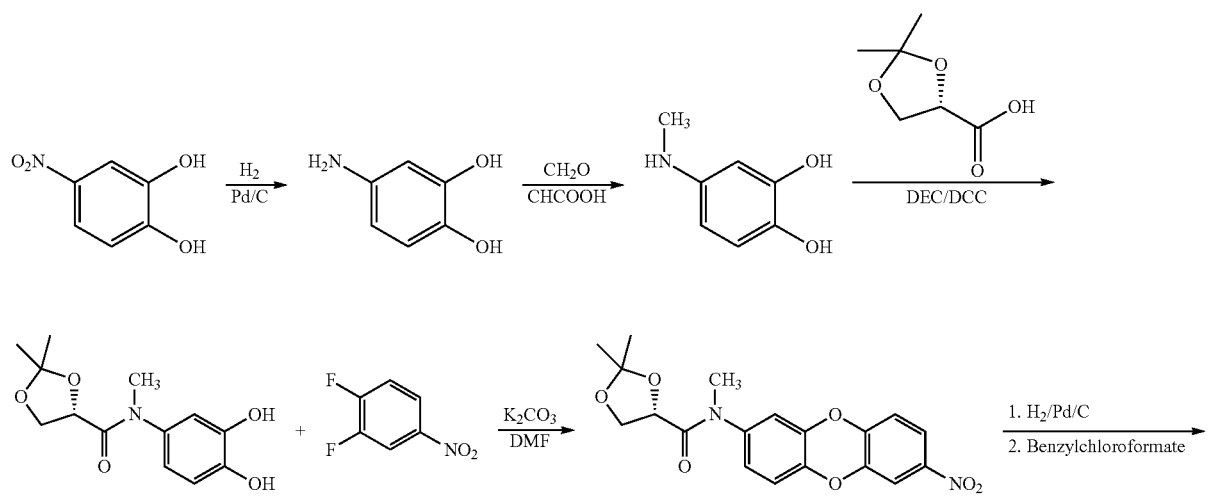

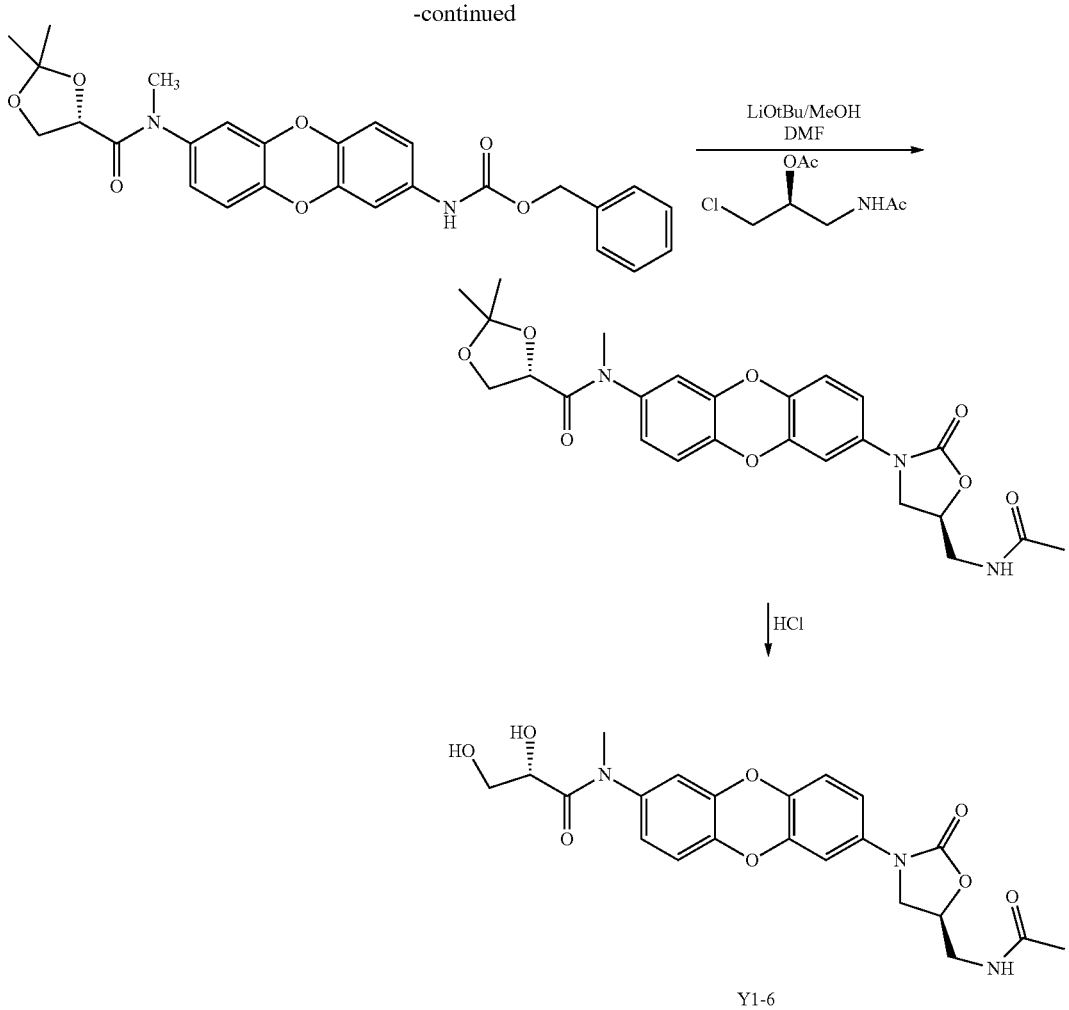

Schemes 9 and 10 are used to synthesize the Y2 series of compounds. All of these compounds have a phenoxazine ring in place of the dibenzodioxin ring. The unsymmetrical difluoronitro compound employed in the first step of Scheme 10 is a known compound and is synthesized following the literature procedure. Choy et al. "Development of a Synthesis For a Long-Term Oxazolidinone Antibacterial," *Org Process Res Dev* 2008, 12(5):884-887. The second step (intramolecular amide formation) is accomplished using a recently published procedure for coupling acids with electron deficient amines. Due-Hansen et al. "A protocol for amide bond formation with electron deficient amines and sterically hindered substrates," *Organic & Biomolecular Chem* 2016, 14(2):430-433.

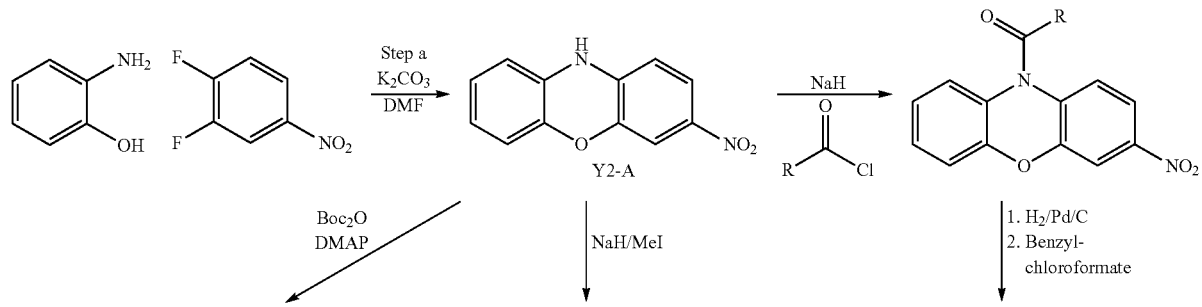

Scheme 9

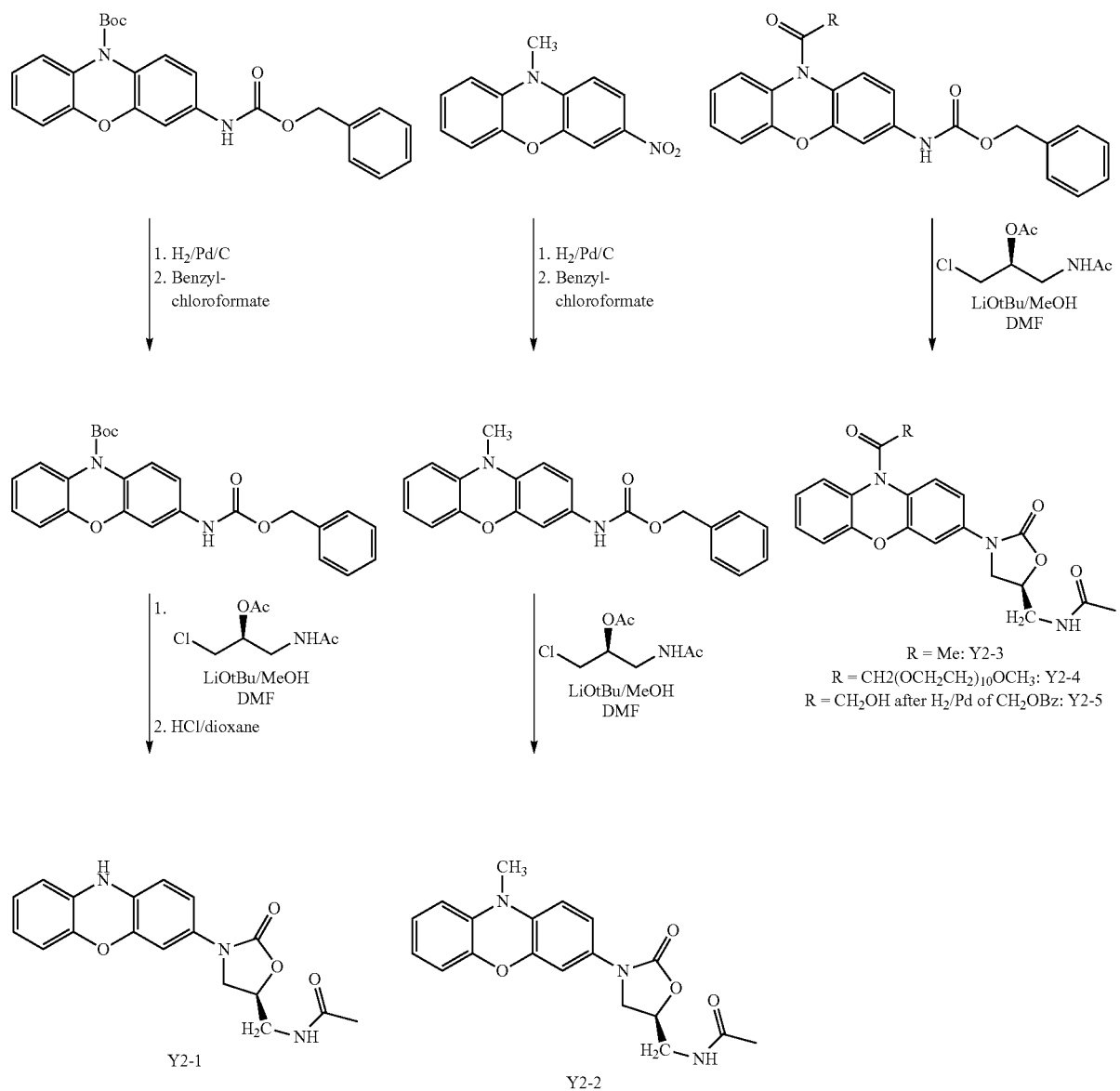
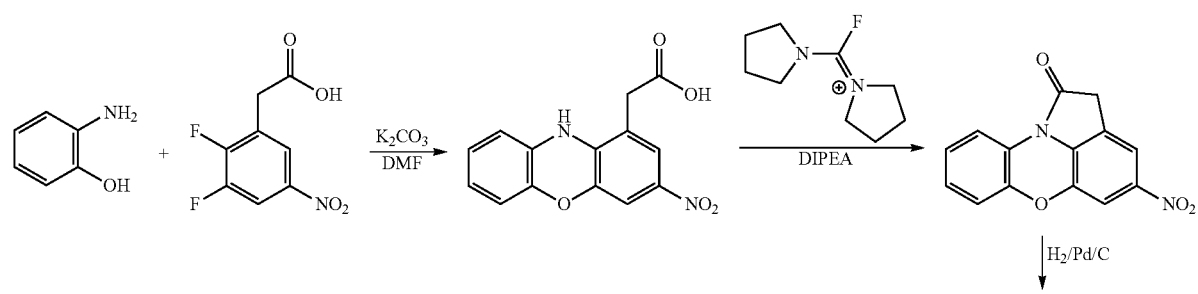

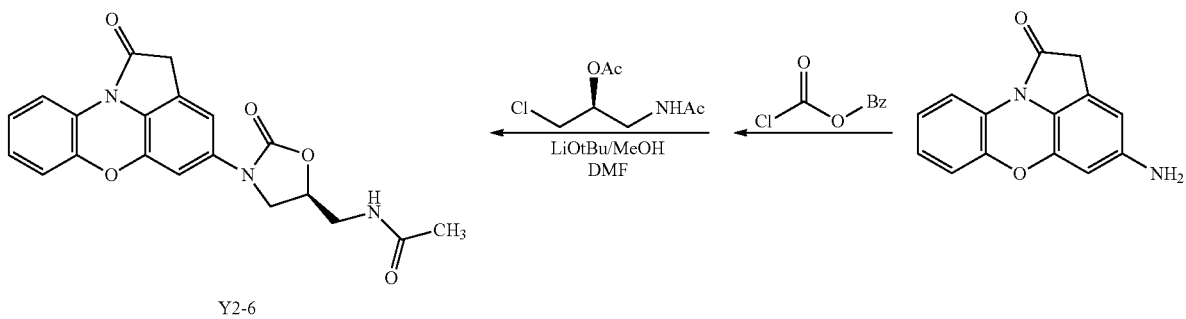

The Y3 series of compounds are fabricated by two different routes. The first group of compounds are benzodioxin-based oxazolidinones with fluorine substituents. The first two exemplary compounds are based on commercially available fluoro-substituted catechols and utilize synthetic methodology used for T145.

The route is shown in Scheme 11. Because the starting diols are symmetrically substituted, the compounds are formed as racemic mixtures.

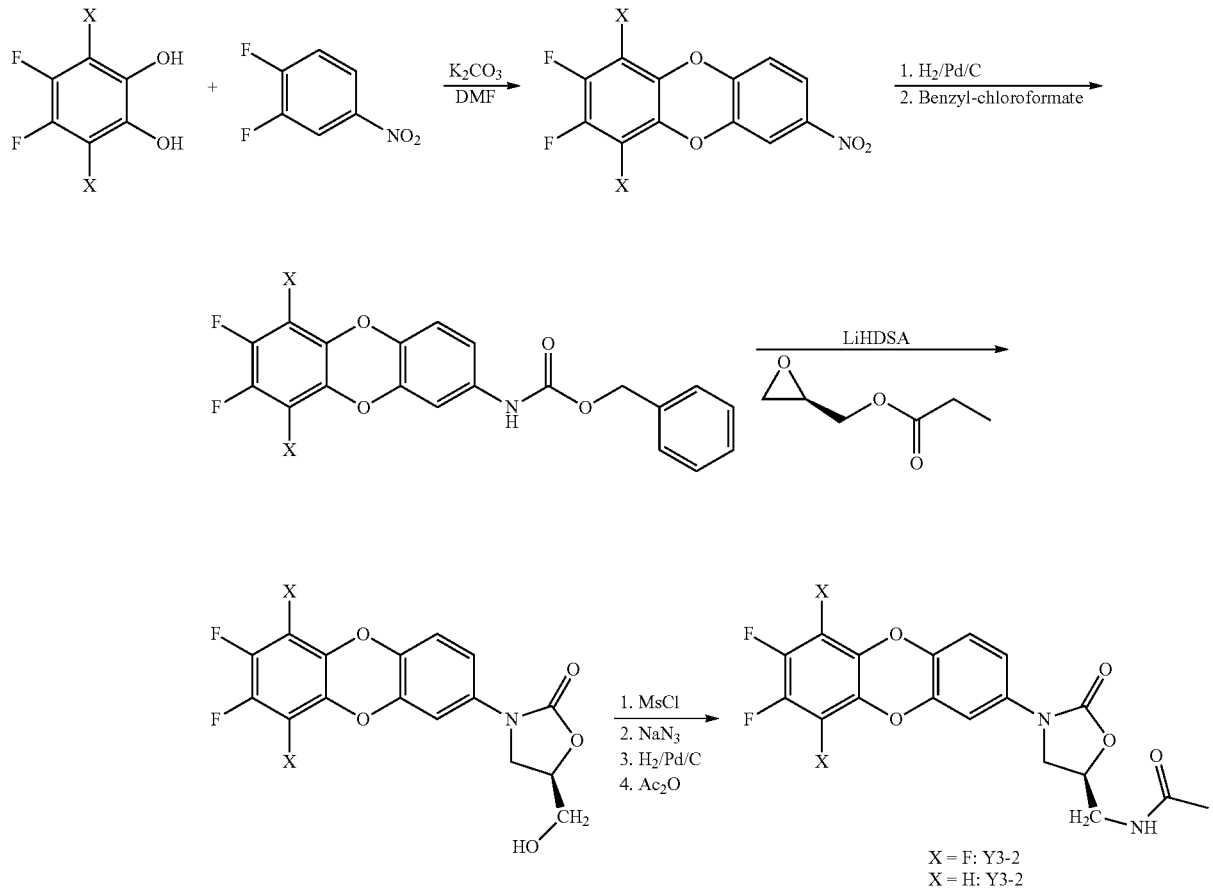

The synthesis of Y3-3 is shown in Scheme 12 and utilizes a newly developed reagent to attach the difluoromethylthio group. See Zhu et al. "A Two-Step, One-Pot, and Multigram-Scale Synthesis of N-Difluoromethylthiophthalimide," *Organic Process Research & Development* 2017, 21(9): 1383-1387.

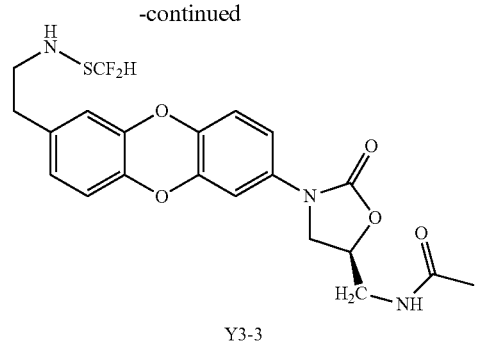

Y3-3

The final set of compounds, Y3-3, Y3-4 and Y3-5, attach biochemically relevant groups.

The synthetic routes all start with compound Y1-3 and are shown in Scheme 13. Compounds Y3-4 and Y3-5 incorporate tri-peptides that are commercially available and are readily attached by typical peptide coupling methodology. The methodology to synthesize the enantiobactin sidephore portion (with carboxylic acid, see Scheme 13) is well documented. See Zheng et al. "Siderophore-mediated cargo delivery to the cytoplasm of *Escherichia coli* and *Pseudomonas aeruginosa*: syntheses of monofunctionalized enterobactin scaffolds and evaluation of enterobactin-cargo conjugate uptake," *J. Amer. Chem. Soc.* 2012, 134(44): 18388-18400.

Scheme 12

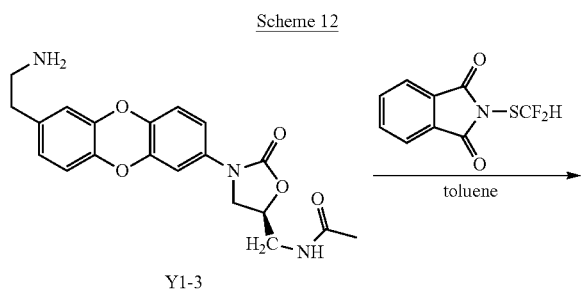

Scheme 13

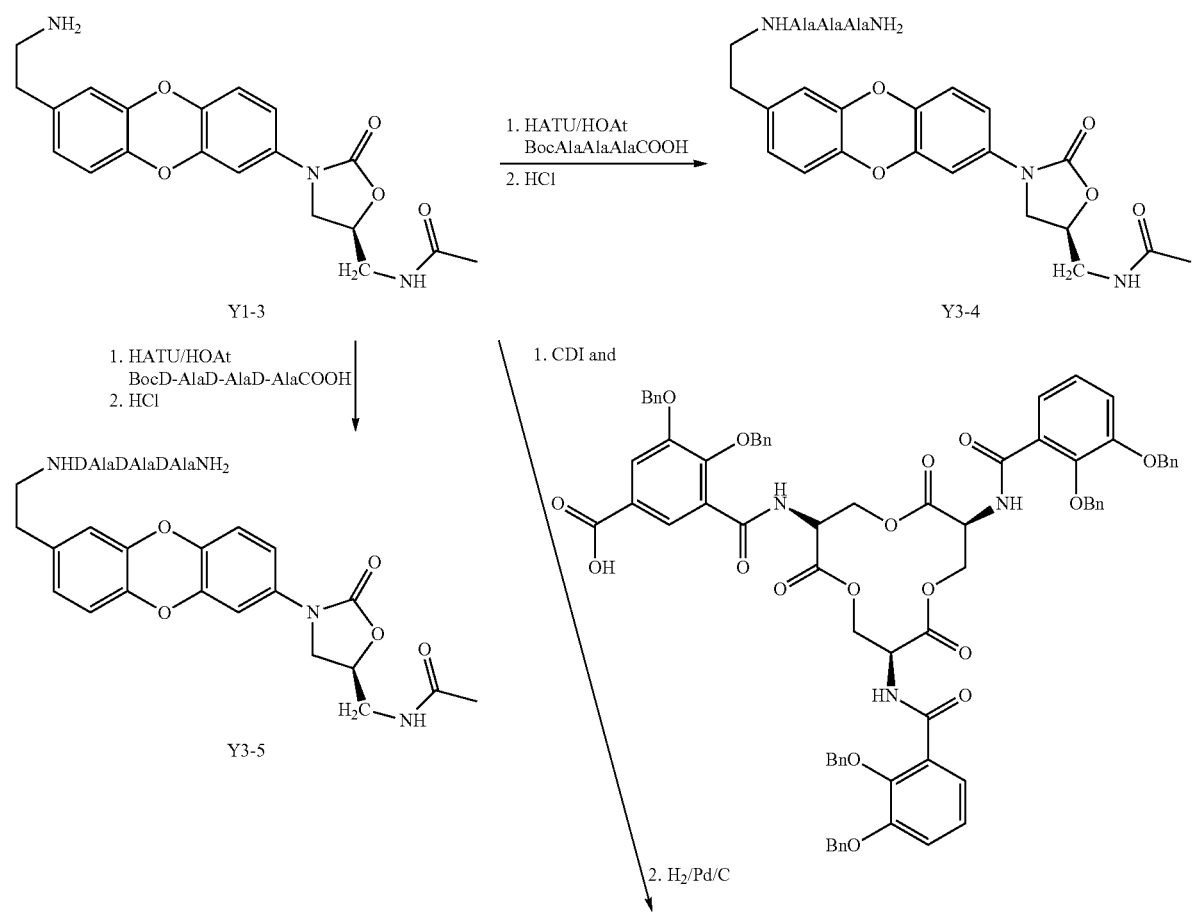

-continued

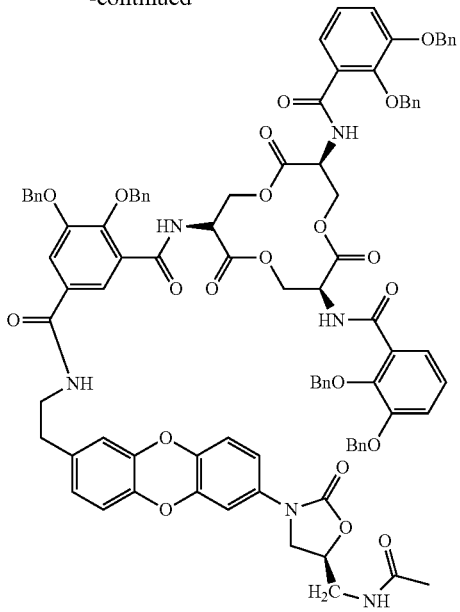

Y3-6

T145, shown below, is a novel oxazolidinone. Linezolid, an oxazolidinone, initially labeled as U-100766, is a Food and Drug Administration approved antibacterial that is used for treatment of a wide range of bacterial pathogens. Spellberg et al. "The epidemic of antibiotic-resistant infections: a call to action for the medical community from the Infectious Diseases Society of America," Clinical infectious diseases: an official publication of the Infectious Diseases Society of America, 46 (2008) 155-164. Oxazolidinones have a common 2-oxazolidone ring and inhibit initiation of protein synthesis by preventing formation of ribosome and N-formylmethionyl-tRNA complex. Boucher et al. "Bad bugs, no drugs: no ESKAPE! An update from the Infectious Diseases Society of America," Clinical infectious diseases: an official publication of the Infectious Diseases Society of America, 48 (2009) 1-12.

Resistance to oxazolidinones generally results from a mutation in 23S rRNA which supports its mechanism of action, or due to activity of efflux pumps. Toxicities associated with long term use of linezolid has spawn interest in newer oxazolidinones that improve on safety profile without compromising potency. See Kloss, et al. "Resistance mutations in 23 S rRNA identify the site of action of the protein synthesis inhibitor linezolid in the ribosomal peptidyl transferase center," *J. Mol. Biol*, 294 (1999) 93-101; Saager et al. "Molecular characterisation of linezolid resistance in two vancomycin-resistant (VanB) *Enterococcus faecium* isolates using pyrosequencing," *Eur. J. Clin Microbiol. & Inf. Diseases*: official publication of the European Society of Clinical Microbiology, 27 (2008) 873-878; and Schumacher et al. "Intracellular accumulation of linezolid in *Escherichia coli, Citrobacter freundii* and *Enterobacter aerogenes*: role of enhanced efflux pump activity and inactivation," *J. of Antimicrob. Chemotherapy*, 59 (2007) 1261-1264. The initial work on T145 only measured its antibacterial activity against *S. aureus*. Here, we have investigated the activity of T145 against ESKAPE pathogens and *Mycobacterium abscessus* (Mab), *Mycobacterium avium* (Mav) and Mtb, the pathogen that causes tuberculosis (TB). We have studied two rifampin mono-resistant strains in addition to its parent drug sensitive strain. Although the World Health Organization declared TB a global health priority more than 20 years ago, this year it increased its estimate of death from this disease to 1.5 million making it the most dangerous bacterial infectious disease in the world. Emergence of multiple- and extensively-drug resistant strains of Mtb in many regions of the world clearly demonstrates that our efforts to innovate new agents against this pathogen have been inadequate. Another emerging crisis is the increasing incidence of drug resistance in ESKAPE pathogens, often in community and hospital settings. This has meant added risk of acquiring potentially incurable infections in health care settings.

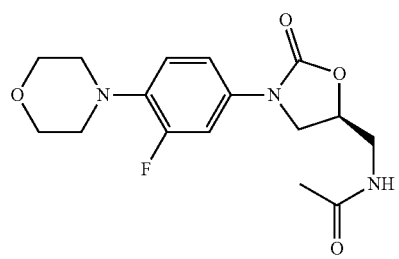

Linezolid

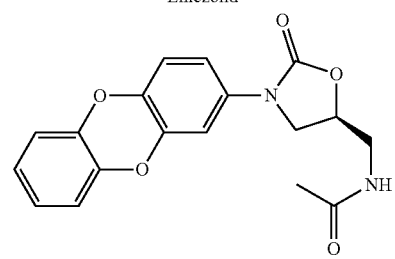

T145

The following strains were used: Mtb H37Rv, Mtb 115R, Mtb 124R, Mab ATCC 19977, Mav 104 (isolated from an adult AIDS patient in Southern California in 1983), *A. baumannii* 6M-1b (an environmental isolate), *A. baumannii* ATCC 19606, *A. baumannii* ACBA (isolated from patient at the Johns Hopkins Hospital) *E. faecalis* ATCC 19433, methicillin-sensitive *S. aureus* ATCC 29213, *E. cloacae* ATCC 13047, *K. pneumoniae* ATCC 35657 and *P. aeruginosa* PA 14. *A. baumannii* 6M-1b was recovered from Monocacy River near Frederick, Md., which is part of the upper watershed of the Chesapeake Bay. It was speciated using a validated MALDI-TOF MS assay (Bruker Micro-Flex LT mass spectrometer and Bruker Biotyper software and existing database (version 2.0)). See Tan et al. "Prospective evaluation of a matrix-assisted laser desorption ionization-time of flight mass spectrometry system in a hospital clinical microbiology laboratory for identification of bacteria and yeasts: a bench-by-bench study for assessing the impact on time to identification and cost-effectiveness," *J. of Clin. Microbiol.* 50 (2012) 3301-3308. The log confidence score was >1.9, which is in the acceptable range for identification to the species level. In addition, a biochemical chart was also done (API 20NE, BioMerieux) which identified the isolate as *A. baumannii*. The API 20 NE is used for identification of non-enteric gram negative rods. Mtb 115R and 124R are mono-rifampin resistant laboratory isolates (from Dr. Eric Nuermberger, Johns Hopkins University) Rosenthal, et al. "Dose-ranging comparison of rifampin and rifapentine in two pathologically distinct murine models of tuberculosis," *Antimicrobial Agents and Chemotherapy*, 56 (2012) 4331-4340. The rifampin minimum inhibitory concentration for the two strains were assessed in this study using broth dilution assay and were determined to be 4.0 and 128 µg/ml, respectively. Mtb H37Rv is the parent strain for 115R and 124R. Mtb, May and Mab were grown in Middlebrook 7H9 broth (Difco), containing 0.5% glycerol, 10% oleic acid-albumindextrose-catalase (OADC) and 0.05% Tween 80 or on Middlebrook 7H10 agar, 37° C. *A. baumannii, E. faecalis, S. aureus, E. cloacae, K. pneumoniae* and *P. aeruginosa* were grown in cation-adjusted Mueller-Hinton broth (Becton-Dickinson). Liquid cultures were grown with constant shaking, 220 RPM, 37° C. Meropenem, doripenem, faropenem, biapenem, tebipenem, clarithromycin and isoniazid were commercially acquired (Sigma-Aldrich). T145 was synthesized in the laboratory to a purity of >99%.

Minimum inhibitory concentration ($MIC_{90}$) for Mtb was determined using standard broth macrodilution in 15-ml sterile conical tubes containing 2.5 ml of 7H9 broth. Standard broth microdilution method (using 96-well plates) was used for other organisms as per Clinical and Laboratory Standard Institute (CLSI) recommendations. Middlebrook 7H9 broth was used for Mab, May and Mtb and cation-adjusted Mueller-Hinton broth (Becton-Dickinson) was used for other organisms as per CLSI guidelines See Gavan and Town, "A microdilution method for antibiotic susceptibility testing: an evaluation," *Amer. J. Clin. Path*, 53 (1970) 880-885 and Desmond, "Susceptibility Testing of Mycobacteria, Nocardiae and Other Aerobic Actinomycetes," Clinical Laboratory Standard Institute, M24-A2 (2011). In summary, $10^5$ bacilli grown to exponential phase in liquid medium were inoculated into each well containing drug at two fold dilutions ranging from 64 µg/ml to 0.03 µg/ml. Growth medium alone and without drug but inoculated with $10^5$ bacilli were included as negative and positive controls, respectively. Appropriate drugs (isoniazid for Mtb, doripenem for Mab, clarithromycin for May and meropenem for *A. baumannii, E. faecalis, S. aureus, E. cloacae, K. pneumoniae* and *P. aeruginosa*) were included as positive control for growth inhibition. Growth was evaluated by visual inspection for presence of bacterial pellet following incubation (at 35° C., 18 hours for *A. baumannii, E. faecalis*, methicillin-resistant *S. aureus, E. cloacae, K. pneumoniae* and *P. aeruginosa*, fourteen days for Mtb at 37° C., 7 days, 37° C. for May and at 30° C., 3 days for Mab) as per CLSI guidelines. (Id.) The first well in which bacterial pellet is absent and therefore growth is not observable is considered the $MIC_{90}$ as per the standard CLSI guidelines. $MIC_{90}$ is expressed as a range spanning two concentrations: the higher concentration represents the lowest concentration at which bacterial growth could not be observed.

Minimum bactericidal concentration (MBC99.9), the minimum concentration of drug that kills 99.9% of bacilli, was determined by extending the broth microdilution assay described above. Surviving bacilli or colony forming units (CFU) in wells in which growth could not be observed were determined by growing them on agar plates containing appropriate growth medium and enumerating CFU (after 2 days, 37° C. for *A. baumannii, E. faecalis, S. aureus* and Mab and 21 days for Mtb). The CFU at the initiation of the study, determined by enumerating live bacilli from initial inoculum on agar plates, is the input inoculum. The concentration of the agent at which 99.9% of the input CFU is killed is reported here as MBC9.9. This assay is a modification of the broth dilution assay and was carried out as previously described. See Hsieh et al. "Synergy assessed by checkerboard. A critical analysis," Diagnostic Microbiology and Infectious Disease, 16 (1993) 343-349. In summary, each well containing $10^5$ CFU received two drugs each in two fold dilutions below their respective $MIC_{90}$. The suspensions are incubated at 37° C. and growth was evaluated as described above. Fractional Inhibitory Concentration (FIC) of a drug in a combination that inhibits bacterial growth is the concentration of the drug in the well divided by $MIC_{90}$ of the drug if used alone. The sum of FIC of each drug in the combination is the FIC index. In each well where bacterial growth was absent, FIC index was calculated and an average FIC index was determined. Drug-drug antagonism was inferred if average FIC index is >4, indifference if >0.5-4.0 and synergy if <0.5.

Each organism was grown as described above to exponential phase, a suspension with optical density ($A_{600nm}$) of 1.0 was prepared and 1.0 ml of this suspension was spread onto each plate containing solid agar with growth media that was supplemented with T145 at 4-20x respectively.

$MIC_{90}$.: Five plates were used for each concentration of T145 studied. Colonies that grew at 37° C. (>2-3 days of incubation for *S. aureus* and at least 21 days for Mtb) were enumerated as spontaneous mutants resistant to T145. Colonies that grew on medium lacking T145 were enumerated as input CFU. The number of resistant mutants as a fraction of the input CFU inoculum was calculated as the frequency of spontaneous mutants resistant to T145.

Synthesis of T145 has been described in an earlier publication. Ebner et al. "Synthesis of novel oxazolidinone antimicrobial agents," *Bioorganic & Medicinal Chemistry*, 16 (2008) 2651-2656. We synthesized a derivative of T145, labeled hereafter as T197. The rationale behind synthesizing and testing T197 was to determine the effect of adding an electron donating substituent to the benzodioxin ring. The methoxy group will also change the steric nature of the ring, which may affect its binding to its target(s). The synthetic route to T197 (an equal mixture of 9a and 9b) is shown below and follows the same synthetic strategy used to synthesize T145:

Scheme 14: Synthetic route used to make T197.
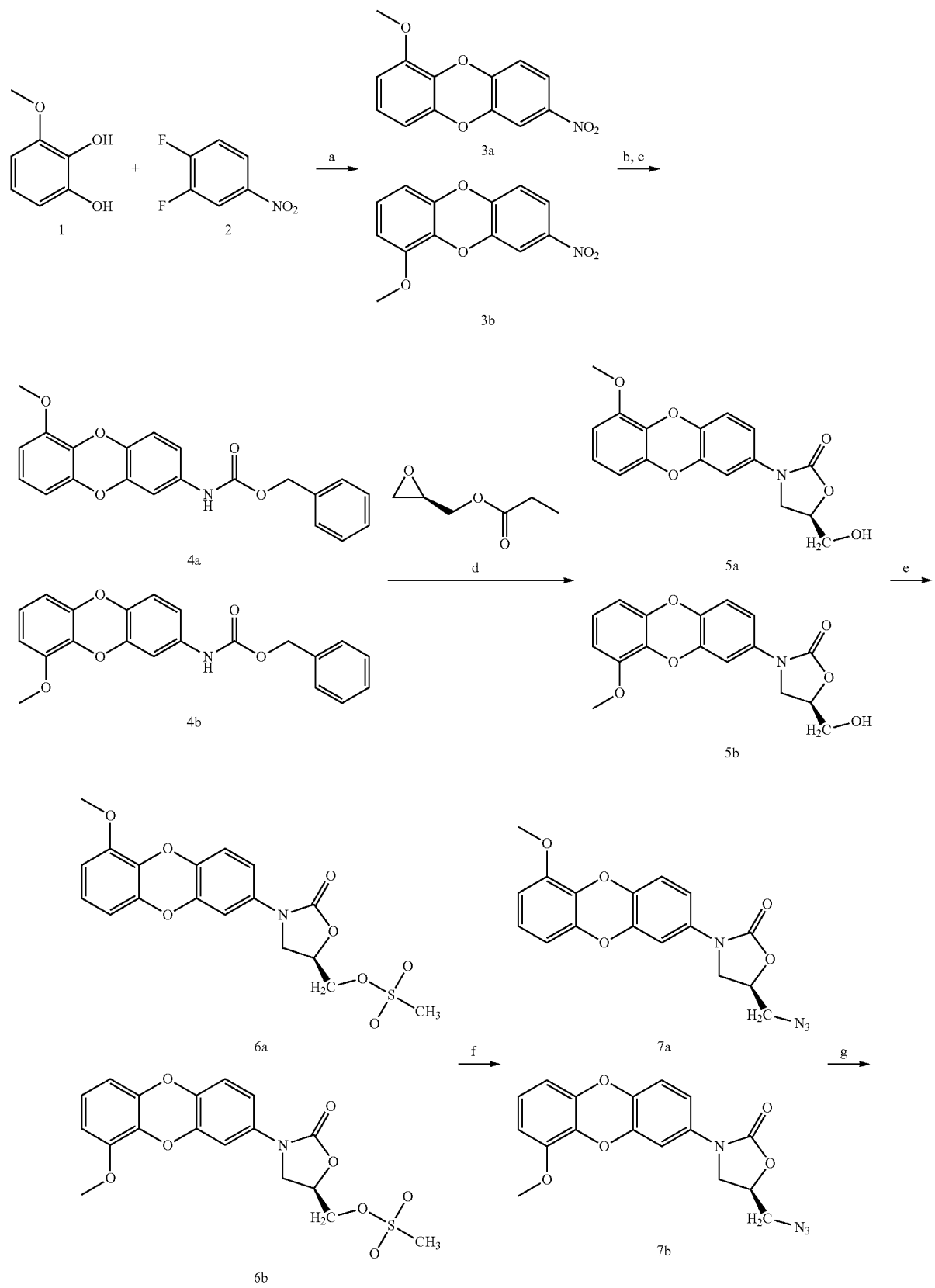

-continued

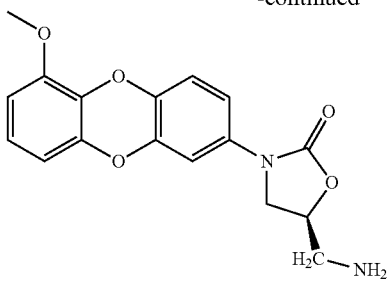

8a

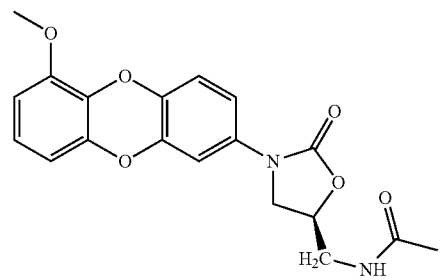

9a h →

8b

9b

Reagents and conditions: a) K₂CO₃, 80:30 DMF: toluene, reflux; b) H₂, 10% Pd/C (50 bar, 50° C.); c) TEA, THF, room temperature; d) THF, n-BuLi, 78° C.; e) methanesulfonyl chloride, TEA, DCM, 0° C.; f) sodium azide, DMF, microwave 80° C. for 1 h; g) H₂, 10% Pd/C (30 bar, 30° C.); h) acetic anhydride, pyridine, room temperature.

Antimicrobial Potency:

We assessed antimicrobial potencies of T145 and T197 against gram negatives *K. pneumoniae, A. baumannii, P. aeruginosa* and *E. cloacae*, gram positives *E. faecalis*, and *S. aureus*, and acid fast pathogens Mab, May and Mtb by determining $MIC_{90}$ and MBC9.9. Linezolid, an oxazolidinone that is clinically used for treatment of bacterial infections, was used as a control. Meropenem, one of the most potent antimicrobial available in clinic today was also included as an additional control in this study. Rhomberg and Jones, "Antimicrobial spectrum of activity for meropenem and nine broad spectrum antimicrobials: report from the MYSTIC Program (2002) in North America," *Diagnostic Microbiology and Infectious Disease*, 47 (2003) 365-372.

T145 exhibited potent activity against growth of gram positive pathogens *S. aureus* and *E. faecalis* and Mtb, including two strains that exhibit low and high levels of resistance to rifampicin (Table 1). T145 displayed no activity against the gram negative pathogens *E. cloacae, K. pneumoniae* and *P. aeruginosa* and non-tuberculosis mycobacteria Mab and May.

We evaluated three axenic isolates of *A. baumannii* for their susceptibilities against T145 and T197. *A. baumannii* 6M-1b is an environmental strain; 19606 is an ATCC typed strain and ACBA is a recent clinical strain. The environmental strain 6M-1b displayed sensitivity to T145, T197, linezolid and meropenem with a $MIC_{90}$ of 0.25-4.0 (Table 1). Next, strain ATCC 19606 was marginally susceptible to T145 only ($MIC_{90}$=32-64 µg/ml). With an MIC90 of >64 µg/ml for T145, T197, linezolid and meropenem, the patient isolate ACBA was most resistant among the three strains. The environmental strain of *A. baumannii* likely was not exposed to oxazolidinones and consequently was never under selective pressure of this agent. The patient isolate ACBA is likely to have the most exposure to drugs amongst the three strains. This data suggests that an increasing exposure to drugs has allowed *A. baumannii* to develop considerable resistance to evolved oxazolidinones T145 and T197.

TABLE 1

Minimum inhibitory concentrations ($MIC_{90}$) of T145 and T197 in µg/ml.

| Organism | $MIC_{90}$ (µg/ml) | | | |
| --- | --- | --- | --- | --- |
| | T145 | T197 | Linezolid | Meropenem |
| Gram negatives | | | | |
| *Acinetobacter baumannii* 6M-1b | 0.25-0.50 | 2-4 | 0.25-0.50 | 1-2 |
| *Acinetobacter baumannii* ATCC 19606 | 32-64 | >64 | >64 | >64 |
| *Acinetobacter baumannii* ACBA | >64 | >64 | >64 | >64 |
| *Enterobacter cloacae* | >64 | >64 | >64 | 0.13-0.25 |
| *Klebsiella pneumoniae* | >64 | >64 | 16-32 | <0.06 |
| *Pseudomonas aeruginosa* | >64 | >64 | >64 | 0.25-0.50 |
| Gram positives | | | | |
| *Staphylococcus aureus* | 0.5-1.0 | 16-32 | 1-2 | 0.06-0.13 |
| *Enterococcus faecalis* | 0.25-0.50 | 8-16 | 1-2 | 4-8 |

TABLE 1-continued

Minimum inhibitory concentrations (MIC$_{90}$) of T145 and T197 in µg/ml.

| Organism | MIC$_{90}$ (µg/ml) | | | |
|---|---|---|---|---|
| | T145 | T197 | Linezolid | Meropenem |
| Mycobacteria | | | | |
| *Mycobacterium tuberculosis* H37Rv | 0.5-1.0 | 8-16 | 0.2-2.0 | 4-8 |
| *Mycobacterium tuberculosis* 115R | 0.5-1.0 | 8-16 | 0.25-0.5 | 8-16 |
| *Mycobacterium tuberculosis* 124R | 0.5-1.0 | 4-8 | 0.25-0.5 | 8-16 |
| *Mycobacterium abscessus* | >64 | >64 | ND | >64 |
| *Mycobacterium avium* | >64 | >64 | ND | >64 |

Data shown in this table were verified with two repeats of MIC determination.
Meropenem and linezolid were used as controls, ND = not done.

It is noteworthy that potency of T145 is several fold superior to meropenem against *E. faecalis* and Mtb. The 0.5-1.0 µg/ml MIC$_{90}$ of T145 for Mtb H37Rv, and rifampicin mono-resistant strains 115R and 124R, is comparable to 0.5-2.0 µg/ml MIC$_{90}$ of linezolid, a clinically used oxazolidinone. See Rodriguez et al. "In vitro activity of moxifloxacin, levofloxacin, gatifloxacin and linezolid against *Mycobacterium tuberculosis*," *Intl J. Antimicrobial Agents*, 20 (2002) 464-467. Today linezolid is one of the alternate drugs used for treatment of multi- and extensively-resistant tuberculosis based on its potency to treat Mtb infections. Fortun et al. "Linezolid for the treatment of multidrug-resistant tuberculosis," *J. Antimicrobial Chemotherapy*, 56 (2005) 180-185. Clinical utility of T145 will be largely determined by its pharmacokinetic, pharmacodynamics and toxicity characteristics. T197, a derivative of T145, displayed antimicrobial activity against *A. baumannii* 6M-1b, *S. aureus*, *Enterococcus faecalis* and Mtb, but its potencies were several fold inferior to T145 (Table 1). It appears that the methoxy substituent that differentiates it from T145 decreases the antibacterial activity. It is possible that isomers 9a and 9b have different antibacterial activities but even if one had no activity and the other isomer all the activity, the one with all the activity would not be as active as T145. Determining which isomer is more active requires separation of the isomers and is currently being pursued. Also the position of the group on the ring will be varied in future work to determine if it is a steric or electronic effect causing this reduced activity.

To further investigate the antimicrobial potency of T145 we determined MBC99.9 for Mtb H37Rv, *E. faecalis* and *S. aureus*. For this, each pathogen was incubated in the presence of T145 at 1, 2, 4 and 8 times respective MIC$_{90}$ and the number of surviving bacilli were determined by enumerating CFU. T145 exhibited bactericidal activity against Mtb with MBC99.9 of 2 µg/ml. *E. faecalis* and *S. aureus* grew confluently on solid medium containing up to 8 times the MIC$_{90}$ of T145. Based on the lack of observable difference in CFU at and up to 8 times MIC$_{90}$, we conclude that T145 is bacteriostatic against *E. faecalis* and *S. aureus*. Linezolid also exhibits bacteriostatic activity against *S. aureus*. Zurenko et al. "In vitro activities of U-100592 and U-100766, novel oxazolidinone antibacterial agents," *Antimicrobial Agents and Chemotherapy*, 40 (1996) 839-845.

As a therapeutic agent, a drug becomes ineffective for treatment of infections that develop resistance against it. Therefore, the frequency at which spontaneous mutation(s) that render a pathogen resistant to a drug arise is a measure of the longevity of the drug. We subjected Mtb, *E. faecalis* and *S. aureus* to T145 at 5x-60x their respective MIC$_{90}$ to determine the frequency of spontaneous resistant mutants. We were able to isolate Mtb mutants after 5 weeks of incubation at 5x and 10xMIC$_{90}$ of T145 and conclude that spontaneous mutations that confer resistance to T145 arise at a frequency of $4.0 \times 10^{-8}$. *E. faecalis* and *S. aureus* did not form classical distinct single colonies on agar plates containing T145. We consistently observed a thin semi-transparent layer atop the agar, which we determined was the initial 1 ml culture deposited on it, on every plate that contained T145 at concentrations up to 60xMIC$_{90}$. Repeat attempts to select spontaneous mutants failed to produce distinct colonies. We hypothesize that T145 is bacteriostatic against *E. faecalis* and *S. aureus* at up to 60x respective MIC$_{90}$ and prevents selection of spontaneous resistant mutants. To test this hypothesis, we scraped the dried semi-transparent layer and transferred to fresh medium. The recovered organisms grew consistently in liquid broth lacking T145 but failed to grow in its presence at its MIC$_{90}$.

Carbapenems are a sub-class of β-lactams and derive their antimicrobial potency by inhibiting peptidoglycan biosynthesis. C. Walsh, "Antibiotics: Actions, Origins, Resistance," ASM Press, Washington D.C., © 2003; ISBN 978-1555812546. We hypothesized that inhibition of two essential pathways, namely protein synthesis by T145 and peptidoglycan biosynthesis by carbapenems, may result in synergistic killing of bacterial pathogens. To evaluate if synergy (or indifference or antagonism) in antimicrobial activity exists between T145 and carbapenems, we used the checkboard titration assay (Hsieh et al. "Synergy assessed by checkerboard. A critical analysis," *Diagnostic Microbiology and Infectious Disease*, 16 (1993) 343-349) and subjected *E. faecalis* and *S. aureus* to combination of the two agents, each at defined concentrations ranging from 1xMIC$_{90}$ to $\frac{1}{16}$xMIC$_{90}$. Parenterally administered carbapenem biapenem, an orally bioavailable penam, faropenem and carbapenem tebipenem were studied as representatives of this class of β-lactams. Both *E. faecalis* and *S aureus* are sensitive to these drugs (Table 2).

TABLE 2

In vitro activity of doripenem, biapenem, faropenem and tebipenem against E*nterococcus* 239 *faecalis*, *Staphylococcus aureus* and *Mycobacterium tuberculosis*. Minimum inhibitory 240 concentrations (MIC$_{90}$) in µg/ml are reported here.

| | *Enterococcus faecalis* | *Staphylococcus aureus* | *Mycobacterium tuberculosis* |
|---|---|---|---|
| Biapenem | 0.25-0.50 | 0.007-0.015 | 2.5-5.0 |
| Faropenem | 0.25-0.50 | 0.015-0.03 | 2.5-5.0 |
| Tebipenem | 0.25-0.50 | 0.03-0.06 | 1.25-2.5 |

Kaushik et al. "Carbapenems and Rifampicin Exhibit Synergy Against *Mycobacterium tuberculosis* and *Mycobacte-*

*rium abscessus,*" *Antimicrobial Agents and Chemotherapy*, (October 2015) 59(10): 6561-6567.

Growth inhibition of pathogens was not observed in any wells containing less than ½ $MIC_{90}$ of T145 or carbapenems demonstrating that antibacterial activity of T145 does not synergize with the tested carbapenems. Growth of the organisms was inhibited in wells containing T145 at ⅛ to ½ $MIC_{90}$.

Based on these data we conclude that antimicrobial activity of T145 is indifferent (neither antagonistic nor synergistic) when combined with biapenem, faropenem and tebipenem. We also evaluated if any drug-drug interaction existed between T145 and isoniazid or rifampicin, two drugs that comprise the backbone of tuberculosis treatment today, against Mtb using the checkerboard assay as described above. We did not observe any antagonism or synergy between T145 and isoniazid or rifampicin, and conclude that activity of T145 against Mtb is indifferent to that of isoniazid or rifampicin.

Oxazolidinones are a relatively new class of antibacterials. Only two variants of oxazolidinones, namely linezolid and tedizolid are available for clinical use. Douros et al. "Drug-drug interactions and safety of linezolid, tedizolid, and other oxazolidinones," *Expert opinion on drug metabolism & toxicology,* 11 (2015) 1849-1859. As most drug resistant strains of Mtb isolated from patients are generally sensitive to linezolid, its off-label use to treat drug resistant TB is not uncommon. See, for example, von der Lippe et al. "Efficacy and safety of linezolid in multidrug resistant tuberculosis (MDR-TB)—a report of ten cases," *J. of Infection,* 52 (2006) 92-96. The enthusiasm for oxazolidinones for treatment of Mtb infections, triggered by linezolid, has led to development of novel agents of this class. Multiple studies have concluded that toxicities associated with long term use of linezolid warrant development of additional oxazolidinones that improve on safety without losing potency. See, for example, Villar et al. "Linezolid safety, tolerability and efficacy to treat multidrug- and extensively drug-resistant tuberculosis," *The European Respiratory Journal,* 38 (2011) 730-733. Variants of linezolid have been described in recent years with improved potencies. Sutezolid (PNU-100480) is a more recent oxazolidinone with an in vitro potency against Mtb similar to linezolid. Williams et al. "Promising antituberculosis activity of the oxazolidinone PNU-100480 relative to that of linezolid in a murine model," *Antimicrobial Agents and Chemotherapy,* 53 (2009) 1314-1319. Assessment using a murine model of TB demonstrated that sutezolid is more potent than linezolid and also possesses sterilizing activity, indicating the potential to shorten duration of therapy. Williams et al. "Addition of PNU-100480 to first-line drugs shortens the time needed to cure murine tuberculosis," *Amer. J. Respiratory and Critical Care Medicine,* 180 (2009) 371-376. A recent study has described potent early bactericidal activity of sutezolid in tuberculosis patients. Wallis et al. "Mycobactericidal activity of sutezolid (PNU100480) in sputum (EBA) and blood (WBA) of patients with pulmonary tuberculosis," *PloS One,* 9 (2014) e94462. AZD5847 is another experimental oxazolidinone with a reportedly improved in vitro potency against Mtb. Balasubramanian et al. "Bactericidal activity and mechanism of action of AZD5847, a novel oxazolidinone for treatment of tuberculosis," *Antimicrobial Agents and Chemotherapy,* 58 (2014) 495-502. A direct comparison of linezolid, sutezolid and AZD5847 demonstrated variable activities of the three oxazolidinones against Mtb. Zhang et al. "In vitro and in vivo activities of three oxazolidinones against nonreplicating *Mycobacterium tuberculosis,*" *Antimicrobial Agents and Chemotherapy,* 58 (2014) 3217-3223.

While antibacterial potency and safety profile influence the potential for deployment of a new clinical agent, the frequency at which spontaneous resistant mutants are selected determines the longevity of the agent. A drug that has therapeutically superior potency, limited and tolerable toxicity and minimizes selection of spontaneous resistant mutant is likely to see effective deployment in the clinic. In addition, a simple and inexpensive synthesis of the drug would make it more accessible.

The frequency of Mtb spontaneous mutants resistant to T145 is similar to the frequency, $2\times10^{-4}5\times10^{-9}$, described for linezolid. Hillemann et al. "In vitro-selected linezolid-resistant *Mycobacterium tuberculosis* mutants," *Antimicrobial Agents and Chemotherapy,* 52 (2008) 800-801. With bactericidal activity against Mtb and in vitro potency that matches that of linezolid, T145 is a new oxazodilinone whose further evaluation of safety in clinical use has the potential to provide additional choice among this class of compounds for treatment of not only Mtb infections but also of gram positive pathogens. The potency of T145 against rifampicin resistant Mtb strains adds to its value as a potential agent for treatment of drug resistant TB. A robust program to develop new agent requires availability of multiple variants from which to optimize accessibility, potency, safety and frequency of resistant mutant selection. T145 provides that additional choice.

More generally, the standard broth microdilution assay is used to determine MIC and MBC. See Kaushik et al. "An evolved oxazolidinone with selective potency against *Mycobacterium tuberculosis* and gram positive bacteria," *Bioorg. & Med. Chem. Lett.* 2016, 26(15):3572-3576. Briefly, *M. tuberculosis* H37Rv (ATCC 27294) grown to exponential phase ($A_{600}$~0.6-0.8) will be used to inoculate ~$10^5$ bacilli into each well of microtiter culture plates containing an oxazolidinone at two-fold serial dilution ranging from 32 to 0.06 µg/mL. Cell pellet size is recorded by visual inspection after 14 days of incubation at 37° C. without shaking per CLSI guidelines. Desmond E, "Susceptibility Testing of Mycobacteria, Nocardiae and Other Aerobic Actinomycetes," Clinical Laboratory Standard Institute 2011, M24-A2. $MIC_{90}$ is the first lowest concentration of drug at which *M. tuberculosis* cell pellet cannot be observed. The samples from this well and the next four wells (with higher drug concentrations) are plated on Middlebrook 7H11 agar to enumerate colony forming units (CFU). (Middlebrook 7H11 agar is available commercially from many sources, such as MilliporeSigma, St. Louis, Mo., catalog no. M0428.) The concentration of the drug at which 99.9% of the bacilli die (compared to the input of $10^5$ CFU) is the MBC99.9 for the drug. The CFU data from the sample at MBC will be used to determine frequency of spontaneous mutants as described in Kaushik et al. Both MIC and MBC are important to guide dosing of the oxazolidinones to achieve adequate serum levels (i.e., above MIC and ideally above MBC).

The most promising oxazolidinones are further assessed in the mouse model of TB. The selection of compounds for further in vivo testing is generally guided by three criteria: MIC/MBC (lowest), water solubility (highest) and frequency of resistant mutants (lowest).

In the mouse model, each compound is dissolved in PBS such that a 200 µL bolus administered by oral gavage provides the desired dose. The BALB/c mice Mtb infection model is preferred because this in vivo model was recently validated for dose ranging studies of linezolid. See Tasneen et al. "Contribution of Oxazolidinones to the Efficacy of Novel Regimens Containing Bedaquiline and Pretomanid in a Mouse Model of Tuberculosis," *Antimicrobial Agents and Chemotherapy* 2015, 60(1):270-277. H37Rv, a virulent Mtb strain, grown in 7H9 broth (MilliporeSigma) to log phase is used to infect 4-6 week old mice (male and female in equal numbers) with aerosolized cultures of Mtb such that ~1000 CFU of bacilli are implanted in their lungs. Treatment is initiated 2 weeks after infection. Infected mice are randomized into four dosage groups that will receive each oxazolidinone once daily at the following doses: 10, 25, 50 and 100 mg/kg body weight. These concentrations were chosen from empirical data on linezolid and sutezolid. (See Tasneen et al.) Linezolid and isoniazid will included as positive controls and untreated mice will serve as negative control. Six mice (2/2 male/female) will be sacrificed at the following time points (one day after infection, the day of treatment initiation and at weeks 1 and 3), and bacterial burden in the lungs of mice will be determined by enumerating CFU by plating lung homogenates on Middlebrook 7H11 agar. These first two time points will serve as a reference of bacterial burden at infection and at the time of treatment initiation. At the completion of the study, minimum effective dose (i.e. the dose that prevents further increase in bacterial burden) and minimum bactericidal dose (MBD) are determined for each compound tested.

Pharmaceutical Compositions:

Also disclosed herein are pharmaceutical compositions comprising one or more of the compounds disclosed herein or a pharmaceutically suitable salt thereof as described herein. More specifically, the pharmaceutical composition may comprise one or more of the subject compounds, as well as a standard, well-known, non-toxic pharmaceutically suitable carrier, adjuvant or vehicle such as, for example, phosphate buffered saline, water, ethanol, polyols, vegetable oils, a wetting agent or an emulsion such as a water/oil emulsion. The composition may be in either a liquid, solid or semi-solid form. For example, the composition may be in the form of a tablet, capsule, ingestible liquid or powder, injectible, suppository, or topical ointment or cream. Proper fluidity can be maintained, for example, by maintaining appropriate particle size in the case of dispersions and by the use of surfactants. It may also be desirable to include isotonic agents, for example, sugars, sodium chloride, and the like. Besides such inert diluents, the composition may also include adjuvants, such as wetting agents, emulsifying and suspending agents, sweetening agents, flavoring agents, perfuming agents, and the like.

Suspensions, in addition to the active compounds, may comprise suspending agents such as, for example, ethoxylated isostearyl alcohols, polyoxyethylene sorbitol and sorbitan esters, microcrystalline cellulose, aluminum metahydroxide, bentonite, agar-agar and tragacanth or mixtures of these substances.

Solid dosage forms such as tablets and capsules can be prepared using techniques well known in the art of pharmacy. For example, compounds produced as described herein can be tableted with conventional tablet bases such as lactose, sucrose, and cornstarch in combination with binders such as acacia, cornstarch or gelatin, disintegrating agents such as potato starch or alginic acid, and a lubricant such as stearic acid or magnesium stearate. Capsules can be prepared by incorporating these excipients into a gelatin capsule along with antioxidants and the relevant GLP-1 analog.

For intravenous administration, the GLP analogs may be incorporated into commercial formulations such as Intralipid©-brand fat emulsions for intravenous injection. ("Intralipid" is a registered trademark of Fresenius Kabi A B, Uppsalla, Sweden.) Where desired, the individual components of the formulations may be provided individually, in kit form, for single or multiple use. A typical intravenous dosage of a representative compounds as described herein is from about 0.1 mg to 100 mg daily and is preferably from 0.5 mg to 3.0 mg daily. Dosages above and below these stated ranges are specifically within the scope of the claims.

Possible routes of administration of the pharmaceutical compositions include, for example, enteral (e.g., oral and rectal) and parenteral. For example, a liquid preparation may be administered, for example, orally or rectally. Additionally, a homogenous mixture can be completely dispersed in water, admixed under sterile conditions with physiologically acceptable diluents, preservatives, buffers or propellants in order to form a spray or inhalant. The route of administration will, of course, depend upon the desired effect and the medical state, age, weight, species, etc. of the subject being treated. The dosage of the composition to be administered to the patient may be determined by one of ordinary skill in the art and depends upon various factors such as weight of the patient, age of the patient, immune status of the patient, etc., and is ultimately at the discretion of the medical or veterinary professional administering the treatment.

With respect to form, the composition may be, for example, a solution, a dispersion, a suspension, an emulsion or a sterile powder which is then reconstituted. The composition may be administered in a single daily dose or multiple doses.

The present disclosure also includes treating bacterial infections in mammals, including humans, by administering an bacterial growth-inhibiting amount of one or more of the compounds (or their pharmaceutically suitable salts) described herein. In particular, the compositions of the present invention may be used to treat bacterial infections of any and all description, including tuberculosis infections in humans.

It should be noted that the above-described pharmaceutical compositions may be utilized in connection with non-human animals, both domestic and non-domestic, as well as humans.

EXAMPLES

Experimental Conditions for Synthesis of T197

1-methoxy-7-nitrodibenzo[b,e][1,4]dioxine (3)

3-methoxycatechol (3.00 g, 21.41 mmol) and $K_2CO_3$ (5.92 g, 42.82 mmol) were stirred in 150 mL 80:20 DMF: Toluene. 3,4difluoronitrobenzene (3.41 g, 21.41 mmol) was added dropwise and the reaction mixture was refluxed for 2 h under $N_2$. The reaction mixture was poured over 450 mL ice water causing a yellow precipitate to form. The solid was vacuum filtered and washed with cold acetone, yielding 5.02 g (90%) of a mixture of (3a) and (3b) as a yellow solid. $^1$H NMR (CDCl$_3$, 400 MHz): δ 3.90 (s, 3H), 6.53 (m, 1H), 6.62 (t, J=6.43, 1H), 6.91 (m, 2H), 7.84 (m, 2H).

Benzyl (6-methoxydibenzo[b,e][1,4]dioxin-2-yl) carbamate (4)

A solution of (3) (2.73 g, 10.532 mmol) in 500 mL THF was run through a Thales Nano H-cube Pro equipped with a 10% Pd/C catalyst cartridge at 50 bar and 50° C. (1 mL/min, 100% H2). The resulting colorless solution was concentrated via rotary evaporation, yielding an off-white solid (98% yield). An NMR in CDCl$_3$ showed 100% conversion to the amine. To a solution of the amine compound (1.272 g, 5.549 mmol) in 25 mL THF was added benzyl chloroformate (1.89 g, 11.098 mmol) and triethylamine (0.123 g, 11.098 mmol). After stirring 22 h under $N_2$, the resulting solid was removed via vacuum filtration, diluted with 50 mL diethyl ether, washed with acidic water (3x), and dried over $Na_2SO_4$. The solvent was removed in vacuo yielding a crude brown oil. The oil was purified on a Biotage Isolera One Flash Purification system in 80:20 Hexanes:EtOAc. A mixture of (4a) and (4b) was isolated off the column as 0.645 g (32%) of a white solid. $^1$H NMR (CDCl$_3$, 400 MHz): δ 3.88 (s, 3H), 5.18 (s, 2H), 6.51 (m, 3H), 6.82 (m, 3H), 7.05 (s, 1H), 7.36 (m, 5H).

(R)-5-(hydroxymethyl)-3-(6-methoxydibenzo[b,e][1,4]dioxin-2-yl)oxazolidin-2-one (5)

In a flame-dried round-bottom flask, (4) (0.54 g, 1.49 mmol) was dissolved in 7 mL anhydrous THF. After cooling the reaction mixture to −78° C., 1.0 M n-Butyllithium (1.55 mL, 1.55 mmol) was added dropwise and stirred for 1.5 h. (R)-(−)-glycidyl butyrate (0.22 mL, 1.58 mmol) was added. The solution was allowed to warm to room temperature for 4 h, diluted with EtOAc, washed with saturated NH$_4$Cl (2x) and brine (2x), and dried over Na$_2$SO$_4$. After concentrating in vacuo, the product was triturated with pentane. A tan solid mixture of (5a) and (5b) (0.431 g, 88%) was isolated via vacuum filtration. $^1$H NMR (CDCl$_3$, 400 MHz): δ 3.76 (d, J=11.56, 1H), 3.89 (s, 3H), 3.96 (m, 3H), 4.72 (m, 1H), 6.49 (d, J=8.19, 1H), 6.57 (d, J=8.45, 1H), 6.90 (m, 3H), 7.18 (m, 1H).

(R)-(3-(6-methoxydibenzo[b,e][1,4]dioxin-2-yl)-2-oxooxazolidin-5-yl)methyl methanesulfonate (6)

A solution of (5) (0.505 g, 1.53 mmol) and triethylamine (0.291 g, 2.68) in 40 mL DCM was cooled to 0° C., 30 min. Methanesulfonyl chloride (0.219 g, 1.91 mmol) was added. The reaction was allowed to warm to room temperature for 24 h, diluted with 50 mL DCM, washed with brine (3x) and dried over Na$_2$SO$_4$. The solvent was removed under reduced pressure yielding 0.317 g (51%) of (6a) and (6b) as white crystals. $^1$H NMR (CDCl$_3$, 400 MHz): δ 3.11 (s, 3H), 3.89 (m, 4H), 4.41 (dd, J=11.8, J'=4.12, 1H), 4.49 (dd, J=11.62, J'=3.52, 1H), 4.90 (m, 1H), 6.49 (d, J=8.26, 1H), 6.57 (d, J=8.71, 1H), 6.85 (m, 1.5H), 6.96 (m, 1H), 7.11 (d, J=9.12, 0.4H), 7.17 (d, J=10.64, 1H).

(R)-5-(azidomethyl)-3-(6-methoxydibenzo[b,e][1,4]dioxin-2-yl)oxazolidin-2-one (7)

In a microwave vial, sodium azide (0.506 g, 7.78 mmol) was dripped into a solution of (6) (0.317 g, 0.778 mmol) in 10 mL DMF. The reaction was microwaved at 80° C., 1 h. The reaction mixture was diluted with EtOAc, washed with water (3x) and brine (2x), and dried over Na$_2$SO$_4$. After concentrating in vacuo, an off-white solid of (7a) and (7b) (0.158 g, 57%) remained. $^1$H NMR (CDCl$_3$, 400 MHz): δ 3.59 (dd, J=13.14, J'=4.43, 1H), 3.69 (dd, J=13.1, J'=3.72, 1H), 3.79 (m, 1H), 3.89 (s, 3H), 4.03 (m, 1H), 4.77 (m, 1H), 6.50 (d, J=8.12, 1H), 6.57 (d, J=8.04, 1H), 6.85 (m, 1.55H), 6.97 (m, 1H), 7.17 (m, 1.5H).

(S)-5-(aminomethyl)-3-(6-methoxydibenzo[b,e][1,4]dioxin-2-yl)oxazolidin-2-one (8)

A solution of (7) (0.158 g, 0.446 mmol) in 16 mL THF was run through the H-Cube Pro equipped with a 10% Pd/C catalyst cartridge at 30 bar and 30° C. (1 mL/min, 100% H2). The resulting solution was concentrated in vacuo yielding a mixture of (8a) and (8b) as an off-white solid (0.098 g, 67%). $^1$H NMR (CDCl$_3$, 400 MHz): δ 2.96 (m, 1H), 3.10 (m, 1H), 3.78 (m, 1H), 3.88 (s, 3H), 3.98 (m, 1H), 4.65 (m, 1H), 6.49 (d, J=8.24, 1H), 6.57 (d, J=8.31, 1H), 6.86 (m, 2H), 6.97 (m, 1H), 7.20 (m, 1H).

(S)—N-((3-(6-methoxydibenzo[b,e][1,4]dioxin-2-yl)-2-oxooxazolidin-5-yl)methyl)acetamide (9)

To a solution of (8) (0.098 g, 0.298 mmol) in 10 mL pyridine was added acetic anhydride (0.037 g, 0.358 mmol). The reaction mixture was allowed to stir 21 hr at room temperature. The solvent was removed in vacuo and the crude product was triturated twice with Et$_2$O to remove the excess pyridine. A mixture of (9a) and (9b) were isolated via vacuum filtration as a blush colored solid (0.025 g, 23%). $^1$H NMR (CDCl$_3$, 400 MHz): δ 2.01 (s, 3H), 3.58 (m, 1H), 3.70 (m, 2H), 3.88 (s, 3H), 3.99 (m, 1H), 4.74 (m, 1H), 6.09 (m, 1H), 6.48(ddd, J=8.27, J'=3.98, J''=1.27, 1H), 6.56 (d, J=8.84, 1H), 6.83 (m, 2H), 6.93 (m, 1.5H), 7.07 (dd, J=8.83, J'=2.65, 0.5H), 7.16 (m, 1H).

TABLE 3

Minimum inhibitory concentrations (MIC$_{90}$) of T145 and T197 in µg/ml.

| | MIC$_{90}$ (µg/ml) | | | |
|---|---|---|---|---|
| Organism | T145 | T197 | Linezolid | Meropenem |
| Gram negatives | | | | |
| *Acinetobacter baumannii* 6M-1b | 0.25-0.50 | 2-4 | 0.25-0.50 | 1-2 |
| *Acinetobacter baumannii* ATCC 19606 | 32-64 | >64 | >64 | >64 |
| *Acinetobacter baumannii* ACBA | >64 | >64 | >64 | >64 |
| *Enterobacter cloacae* | >64 | >64 | >64 | 0.13-0.25 |
| *Klebsiella pneumoniae* | >64 | >64 | 16-32 | <0.06 |
| *Pseudomonas aeruginosa* | >64 | >64 | >64 | 0.25-0.50 |
| Gram positives | | | | |
| *Staphylococcus aureus* | 0.5-1.0 | 16-32 | 1-2 | 0.06-0.13 |
| *Enterococcus faecalis* | 0.25-0.50 | 8-16 | 1-2 | 4-8 |
| Mycobacteria | | | | |
| *Mycobacterium tuberculosis* H37Rv | 0.5-1.0 | 8-16 | 0.2-2.0 | 4-8 |
| *Mycobacterium tuberculosis* 115R | 0.5-1.0 | 8-16 | 0.25-0.5 | 8-16 |

TABLE 3-continued

Minimum inhibitory concentrations (MIC$_{90}$) of T145 and T197 in µg/ml.

| Organism | MIC$_{90}$ (µg/ml) | | | |
|---|---|---|---|---|
| | T145 | T197 | Linezolid | Meropenem |
| *Mycobacterium tuberculosis* 124R | 0.5-1.0 | 4-8 | 0.25-0.5 | 8-16 |
| *Mycobacterium abscessus* | >64 | >64 | ND | >64 |
| *Mycobacterium avium* | >64 | >64 | ND | >64 |

Data shown in Table 1 were verified with two repeats of MIC determination.
Meropenem and linezolid were used as controls, ND = not done.

TABLE 4

In vitro activity of doripenem, biapenem, faropenem and tebipenem against *Enterococcus faecalis*, *Staphylococcus aureus* and *Mycobacterium tuberculosis*. Minimum inhibitory concentrations (MIC$_{90}$) in µg/ml are reported.

| | *Enterococcus faecalis* | *Staphylococcus aureus* | *Mycobacterium tuberculosis* |
|---|---|---|---|
| Biapenem | 0.25-0.50 | 0.007-0.015 | 2.5-5.0 |
| Faropenem | 0.25-0.50 | 0.015-0.03 | 2.5-5.0 |
| Tebipenem | 0.25-0.50 | 0.03-0.06 | 1.25-2.5 |

What is claimed is:

1. An oxazolidinone compound of Formula I

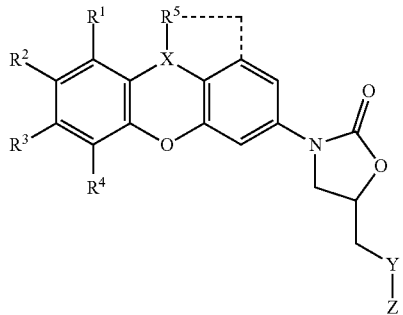

wherein X is —N—; and
R$^5$ is selected from the group consisting of hydrogen, halogen, amino, C$_1$-C$_6$- alkyl, hydroxyl-substituted-C$_1$-C$_6$-alkyl, halo-substituted-C$_1$-C$_6$-alkyl, amino-substituted- C$_1$-C$_6$-alkyl, —C(=O)—C$_1$-C$_6$-alkyl-(O—CH$_2$-CH$_2$)$_{1-16}$—O—C$_1$-C$_6$-alkyl, —C(=O)—OR, —C(=O)R, —C$_1$-C$_6$-alkyl(=O)R, and —C(=O)—NRR, wherein each R is independently hydrogen or C$_1$-C$_6$-alkyl, unsubstituted or substituted with one or more hydroxyl or halo, and the dashed bonds attached to R$^5$ are absent; or R$^5$ is —(C=O)—, in which case X, R$^5$, the dashed bonds, and the carbons to which they are attached define a 5-membered lactam ring;
Y is selected from the group consisting of —N(H)— and —O—;
Z is selected from the group consisting of H, —OH, —C(=O)—OH, —C(=O)—O—C$_1$-C$_6$-alkyl, —C(=O)-amino acid, —C(=O)-polypeptide having from two (2) to fifty (50) residues, an azole, —C(=O)R, —C$_1$-C$_6$-alkyl(=O)R, and —C(=O)—NRR, wherein each R is independently hydrogen or C$_1$-C$_6$-alkyl, unsubstituted or substituted with one or more hydroxyl or halo;

R$^1$, R$^2$, R$^3$, and R$^4$ are independently selected from the group consisting of hydrogen, halogen, amino, C$_1$-C$_6$-alkyl, hydroxyl-substituted-C$_1$-C$_6$-alkyl, halo-substituted-C$_1$-C$_6$-alkyl, amino-substituted-C$_1$-C$_6$-alkyl, —C(=O)—OH, —C(=O)—O—C$_1$-C$_6$-alkyl, -aryl, -heteroaryl, -heterocyclyl, —C$_1$-C$_6$-alkyl-aryl, —C$_1$-C$_6$-alkyl-heteroaryl, —C$_1$-C$_6$-alkyl-heterocyclyl, —C$_1$-C$_6$-alkyl-amino-SCF$_2$R, —C(=O)R, —C$_1$-C$_6$-alkyl(=O)R, and —C(=O)—NRR, wherein each R is independently hydrogen or C$_1$-C$_6$-alkyl unsubstituted or substituted with one or more hydroxyl or halo, -linker-polypeptide having from two (2) to fifty (50) residues, and -linker-siderophore;
provided that not all of R$^1$, R$^2$, R$^3$, and R$^4$ are simultaneously hydrogen; and
salts thereof.

2. An oxazolidinone compound of Formula I

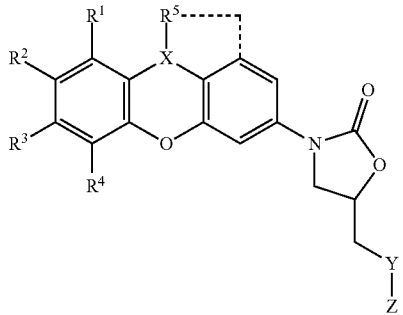

wherein:
X is selected from the group consisting of —N— and —O—;
when X is —O—, R$^5$ and the dotted bonds are absent;
when X is —N—, R$^5$ is selected from the group consisting of hydrogen, halogen, amino, C$_1$-C$_6$-alkyl, hydroxyl-substituted-C$_1$-C$_6$-alkyl, halo-substituted-C$_1$-C$_6$-alkyl, amino-substituted- C$_1$-C$_6$-alkyl, —C(=O)—C$_1$-C$_6$-alkyl-(O—CH$_2$-CH$_2$)$_{1-16}$—O—C$_1$-C$_6$-alkyl, —C(=O)—OR, —C(=O)R, —C$_1$-C$_6$-alkyl(=O)R, and —C(=O)—NRR, wherein each R is independently hydrogen or C$_1$-C$_6$-alkyl, unsubstituted or substituted with one or more hydroxyl or halo, and the dashed bonds attached to R$^5$ are absent; or R$^5$ is —(C=O)—, in which case X, R$^5$, the dashed bonds, and the carbons to which they are attached define a 5-membered lactam ring;
Y is —O—;
Z is selected from the group consisting of H, —OH, —C(=O)—OH, —C(=O)—O—C$_1$-C$_6$-alkyl, —C(=O)-amino acid, —C(=O)-polypeptide having from two (2) to fifty (50) residues, an azole, —C(═O)R, —C$_1$-C$_6$-alkyl(═O)R, and —C(═O)—NRR, wherein each R is independently hydrogen or C$_1$-C$_6$-alkyl, unsubstituted or substituted with one or more hydroxyl or halo;

R$^1$, R$^2$, R$^3$, and R$^4$ are independently selected from the group consisting of hydrogen, halogen, amino, C$_1$-C$_6$-alkyl, hydroxyl-substituted-C$_1$-C$_6$-alkyl, halo-substituted-C$_1$-C$_6$-alkyl, amino-substituted-C$_1$-C$_6$-alkyl, —C(═O)—OH, —C(═O)—O—C$_1$-C$_6$-alkyl, -aryl, -heteroaryl, -heterocyclyl, -C$_1$-C$_6$-alkyl-aryl, —C$_1$-C$_6$-alkyl-heteroaryl, —C$_1$-C$_6$-alkyl-heterocyclyl, —C$_1$-C$_6$-alkyl-amino-SCF$_2$R, —C(═O)R, —C$_1$-C$_6$-alkyl(═O)R, and —C(═O)—NRR, wherein each R is independently hydrogen or C$_1$-C$_6$-alkyl unsubstituted or substituted with one or more hydroxyl or halo, -linker-polypeptide having from two (2) to fifty (50) residues, and -linker-siderophore;

provided that not all of R$^1$, R$^2$, R$^3$, and R$^4$ are simultaneously hydrogen; and salts thereof.

3. An oxazolidinone compound of Formula I

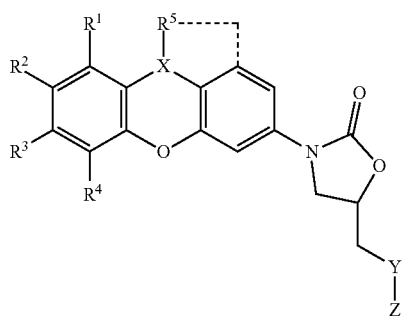

wherein:

X is selected from the group consisting of —N— and —O—;

when X is —O—, R$^5$ and the dotted bonds are absent;

when X is —N—, R$^5$ is selected from the group consisting of hydrogen, halogen, amino, C$_1$-C$_6$-alkyl, hydroxyl-substituted-C$_1$-C$_6$-alkyl, halo-substituted-C$_1$-C$_6$-alkyl, amino-substituted-C$_1$—C$_6$-alkyl, —C(═O)—C$_1$-C$_6$-alkyl-(O—CH$_2$—CH$_2$)$_{1-16}$—O—C$_1$-C$_6$-alkyl, —C(═O)—OR, —C(═O)R, —C$_1$-C$_6$-alkyl(═O)R, and —C(═O)—NRR, wherein each R is independently hydrogen or C$_1$-C$_6$-alkyl, unsubstituted or substituted with one or more hydroxyl or halo, and the dashed bonds attached to R$^5$ are absent; or R$^5$ is —(C═O)—, in which case X, R$^5$, the dashed bonds, and the carbons to which they are attached define a 5-membered lactam ring;

Y is selected from the group consisting of —N(H)— and —O—;

Z is 3-isoxazole, 4-isoxazole, or 5-isoxazole;

R$^1$, R$^2$, R$^3$, and R$^4$ are independently selected from the group consisting of hydrogen, halogen, amino, C$_1$-C$_6$-alkyl, hydroxyl-substituted-C$_1$-C$_6$-alkyl, halo-substituted-C$_1$-C$_6$-alkyl, amino-substituted-C$_1$-C$_6$-alkyl, —C(═O)—OH, —C(═O)—O—C$_1$-C$_6$-alkyl, -aryl, -heteroaryl, -heterocyclyl, —C$_1$-C$_6$-alkyl-aryl, —C$_1$-C$_6$-alkyl-heteroaryl, —C$_1$-C$_6$-alkyl-heterocyclyl, —C$_1$-C$_6$-alkyl-amino-SCF$_2$R, —C(═O)R, —C$_1$-C$_6$-alkyl(═O)R, and —C(═O)—NRR, wherein each R is independently hydrogen or C$_1$-C$_6$-alkyl unsubstituted or substituted with one or more hydroxyl or halo, -linker-polypeptide having from two (2) to fifty (50) residues, and -linker-siderophore;

provided that not all of R$^1$, R$^2$, R$^3$, and R$^4$ are simultaneously hydrogen; and salts thereof.

4. An oxazolidinone compound of Formula I

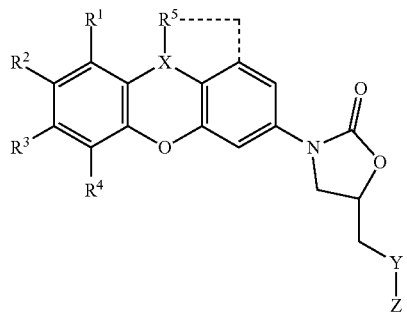

wherein:

X is selected from the group consisting of —N— and —O—;

when X is —O—, R$^5$ and the dotted bonds are absent;

when X is —N—, R$^5$ is selected from the group consisting of hydrogen, halogen, amino, C$_1$-C$_6$-alkyl, hydroxyl-substituted-C$_1$-C$_6$-alkyl, halo-substituted-C$_1$-C$_6$-alkyl, amino-substituted-C$_1$—C$_6$-alkyl, —C(═O)—C$_1$-C$_6$-alkyl-(O—CH$_2$-CH$_2$)$_{1-16}$—O—C$_1$-C$_6$-alkyl, —C(═O)—OR, —C(═O)R, —C$_1$-C$_6$-alkyl(═O)R, and —C(═O)—NRR, wherein each R is independently hydrogen or C$_1$-C$_6$-alkyl, unsubstituted or substituted with one or more hydroxyl or halo, and the dashed bonds attached to R$^5$ are absent; or R$^5$ is —(C═O)—, in which case X, R$^5$, the dashed bonds, and the carbons to which they are attached define a 5-membered lactam ring;

Y is selected from the group consisting of —N(H)— and —O—;

Z is selected from the group consisting of H, —OH, —C(═O)—OH, —C(═O)—O—C$_1$-C$_6$-alkyl, —C(═O)-amino acid, —C(═O)-polypeptide having from two (2) to fifty (50) residues, an azole, —C(═O)R, —C$_1$-C$_6$-alkyl(═O)R, and —C(═O)—NRR, wherein each R is independently hydrogen or C$_1$-C$_6$-alkyl, unsubstituted or substituted with one or more hydroxyl or halo;

R$^1$, R$^3$, and R$^4$ are hydrogen;

R$^2$ is hydroxyl-substituted-C$_1$-C$_6$-alkyl, halo-substituted-C$_1$-C$_6$-alkyl, amino-substituted-C$_1$-C$_6$-alkyl, —C(═O)—OH, —C(═O)R, —C$_1$-C$_6$-alkyl(═O)R, and —C(═O)—NRR, wherein each R is independently hydrogen or C$_1$-C$_6$-alkyl unsubstituted or substituted with one or more hydroxyl or halo; and salts thereof.

5. A pharmaceutical composition comprising a bacterial growth-inhibiting amount of a compound of Formula I

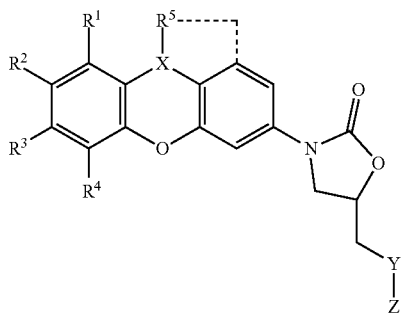

wherein X is —N—; and
R⁵ is selected from the group consisting of hydrogen, halogen, amino, $C_1$-$C_6$-alkyl, hydroxyl-substituted-$C_1$-$C_6$-alkyl, halo-substituted-$C_1$-$C_6$-alkyl, amino-substituted-$C_1$-$C_6$-alkyl, —C(=O)—$C_1$-$C_6$-alkyl-(O—CH$_2$-CH$_2$)$_{1-16}$—O—$C_1$-$C_6$-alkyl, —C(=O)—OR, —C(=O)R, —$C_1$-$C_6$-alkyl(=O)R, and —C(=O)—NRR, wherein each R is independently hydrogen or $C_1$-$C_6$-alkyl, unsubstituted or substituted with one or more hydroxyl or halo, and the dashed bonds attached to R⁵ are absent; or R⁵ is —(C=O)—, in which case X, R⁵, the dashed bonds, and the carbons to which they are attached define a 5-membered lactam ring;
Y is selected from the group consisting of —N(H)— and —O—;
Z is selected from the group consisting of H, —OH, —C(=O)—OH, —C(=O)—O—$C_1$-$C_6$-alkyl, —C(=O)-amino acid, —C(=O)-polypeptide having from two (2) to fifty (50) residues, an azole, —C(=O)R, —$C_1$-$C_6$-alkyl(=O)R, and —C(=O)—NRR, wherein each R is independently hydrogen or $C_1$-$C_6$-alkyl, unsubstituted or substituted with one or more hydroxyl or halo;
R¹, R², R³, and R⁴ are independently selected from the group consisting of hydrogen, halogen, amino, $C_1$-$C_6$-alkyl, hydroxyl-substituted-$C_1$-$C_6$-alkyl, halo-substituted-$C_1$-$C_6$-alkyl, amino-substituted-$C_1$-$C_6$-alkyl, —C(=O)—OH, —C(=O)—O—$C_1$-$C_6$-alkyl, -aryl, -heteroaryl, -heterocyclyl, -$C_1$-$C_6$-alkyl-aryl, —$C_1$-$C_6$-alkyl-heteroaryl, —$C_1$-$C_6$-alkyl-heterocyclyl, —$C_1$-$C_6$-alkyl-amino-SCF$_2$R, —C(=O)R, —$C_1$-$C_6$-alkyl(=O)R, and —C(=O)—NRR, wherein each R is independently hydrogen or $C_1$-$C_6$-alkyl unsubstituted or substituted with one or more hydroxyl or halo, -linker-polypeptide having from two (2) to fifty (50) residues, and -linker-siderophore;
provided that not all of R¹, R², R³, and R⁴ are simultaneously hydrogen; and
pharmaceutically suitable salts thereof;
in combination with a pharmaceutically suitable carrier.

6. A pharmaceutical composition comprising a bacterial growth-inhibiting amount of a compound of Formula I

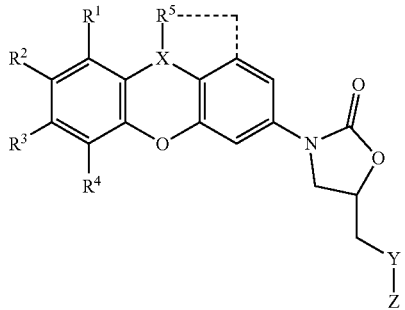

wherein:
X is selected from the group consisting of —N— and —O—;
when X is —O—, R⁵ and the dotted bonds are absent;
when X is —N—, R⁵ is selected from the group consisting of hydrogen, halogen, amino, $C_1$-$C_6$-alkyl, hydroxyl-substituted-$C_1$-$C_6$-alkyl, halo-substituted-$C_1$-$C_6$-alkyl, amino-substituted- $C_1$-$C_6$-alkyl, —C(=O)—$C_1$-$C_6$-alkyl-(O—CH$_2$-CH$_2$)$_{1-16}$—O—$C_1$-$C_6$-alkyl, —C(=O)—OR, —C(=O)R, —$C_1$—$C_6$-alkyl(=O)R, and —C(=O)—NRR, wherein each R is independently hydrogen or $C_1$-$C_6$-alkyl, unsubstituted or substituted with one or more hydroxyl or halo, and the dashed bonds attached to R⁵ are absent; or R⁵ is —(C=O)—, in which case X, R⁵, the dashed bonds, and the carbons to which they are attached define a 5-membered lactam ring;
Y is —O—;
Z is selected from the group consisting of H, —OH, —C(=O)—OH, —C(=O)—O—$C_1$-$C_6$-alkyl, —C(=O)-amino acid, —C(=O)-polypeptide having from two (2) to fifty (50) residues, an azole, —C(=O)R, —$C_1$-$C_6$-alkyl(=O)R, and —C(=O)—NRR, wherein each R is independently hydrogen or $C_1$-$C_6$-alkyl, unsubstituted or substituted with one or more hydroxyl or halo;
R¹, R², R³, and R⁴ are independently selected from the group consisting of hydrogen, halogen, amino, $C_1$-$C_6$-alkyl, hydroxyl-substituted-$C_1$-$C_6$-alkyl, halo-substituted-$C_1$-$C_6$-alkyl, amino-substituted-$C_1$-$C_6$-alkyl, —C(=O)—OH, —C(=O)—O—$C_1$-$C_6$-alkyl, -aryl, -heteroaryl, -heterocyclyl, —$C_1$-$C_6$-alkyl-aryl, —$C_1$-$C_6$-alkyl-heteroaryl, —$C_1$-$C_6$-alkyl-heterocyclyl, —$C_1$-$C_6$-alkyl-amino-SCF$_2$R, —C(=O)R, —$C_1$-$C_6$-alkyl(=O)R, and —C(=O)—NRR, wherein each R is independently hydrogen or $C_1$-$C_6$-alkyl unsubstituted or substituted with one or more hydroxyl or halo, -linker-polypeptide having from two (2) to fifty (50) residues, and -linker-siderophore;
provided that not all of R¹, R², R³, and R⁴ are simultaneously hydrogen; and
pharmaceutically suitable salts thereof;
in combination with a pharmaceutically suitable carrier.

7. A pharmaceutical composition comprising a bacterial growth-inhibiting amount of a compound of Formula I

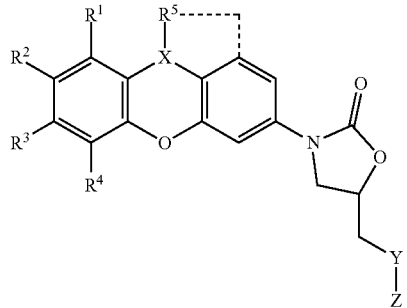

wherein:
X is selected from the group consisting of —N— and —O—;
when X is —O—, R⁵ and the dotted bonds are absent;
when X is —N—, R⁵ is selected from the group consisting of hydrogen, halogen, amino, $C_1$-$C_6$-alkyl, hydroxyl-substituted-$C_1$-$C_6$-alkyl, halo-substituted-$C_1$-$C_6$-alkyl, amino-substituted- $C_1$-$C_6$-alkyl, —C(=O)—$C_1$-$C_6$-alkyl-(O—CH$_2$-CH$_2$)$_{1-16}$—O—$C_1$-$C_6$-alkyl, —C(=O)—OR, —C(=O)R, —C₁-C₆-alkyl(=O)R, and —C(=O)—NRR, wherein each R is independently hydrogen or C₁-C₆-alkyl, unsubstituted or substituted with one or more hydroxyl or halo, and the dashed bonds attached to R⁵ are absent; or R⁵ is —(C=O)—, in which case X, R⁵, the dashed bonds, and the carbons to which they are attached define a 5-membered lactam ring;

Y is selected from the group consisting of —N(H)— and —O—;

Z is 3-isoxazole, 4-isoxazole, or 5-isoxazole;

R¹, R², R³, and R⁴ are independently selected from the group consisting of hydrogen, halogen, amino, C₁-C₆-alkyl, hydroxyl-substituted-C₁-C₆-alkyl, halo-substituted-C₁-C₆-alkyl, amino-substituted-C₁-C₆-alkyl, —C(=O)—OH, —C(=O)—O—C₁—C₆-alkyl, -aryl, -heteroaryl, -heterocyclyl, —C₁-C₆-alkyl-aryl, —C₁-C₆-alkyl-heteroaryl, —C₁-C₆-alkyl-heterocyclyl, —C₁-C₆-alkyl-amino-SCF₂R, —C(=O)R, —C₁-C₆-alkyl(=O)R, and —C(=O)—NRR, wherein each R is independently hydrogen or C₁-C₆-alkyl unsubstituted or substituted with one or more hydroxyl or halo, -linker-polypeptide having from two (2) to fifty (50) residues, and -linker-siderophore;

provided that not all of R¹, R², R³, and R⁴ are simultaneously hydrogen; and pharmaceutically suitable salts thereof;

in combination with a pharmaceutically suitable carrier.

8. A pharmaceutical composition comprising a bacterial growth-inhibiting amount of a compound of Formula I

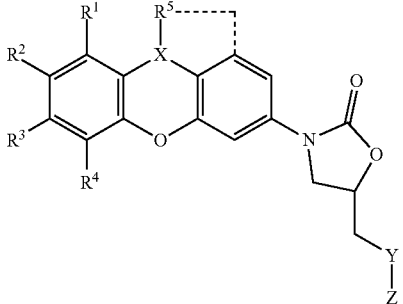

wherein:

X is selected from the group consisting of —N— and —O—;

when X is —O—, R⁵ and the dotted bonds are absent;

when X is —N—, R⁵ is selected from the group consisting of hydrogen, halogen, amino, C₁-C₆-alkyl, hydroxyl-substituted-C₁-C₆-alkyl, halo-substituted-C₁-C₆-alkyl, amino-substituted-C₁-C₆-alkyl, —C(=O)—C₁-C₆-alkyl-(O—CH₂—CH₂)₁₋₁₆—O—C₁-C₆-alkyl, —C(=O)—OR, —C(=O)R, —C₁-C₆-alkyl(=O)R, and —C(=O)—NRR, wherein each R is independently hydrogen or C₁-C₆-alkyl, unsubstituted or substituted with one or more hydroxyl or halo, and the dashed bonds attached to R⁵ are absent; or R⁵ is —(C=O)—, in which case X, R⁵, the dashed bonds, and the carbons to which they are attached define a 5-membered lactam ring;

Y is selected from the group consisting of —N(H)— and —O—;

Z is selected from the group consisting of H, —OH, —C(=O)—OH, —C(=O)—O—C₁-C₆-alkyl, —C(=O)-amino acid, —C(=O)-polypeptide having from two (2) to fifty (50) residues, an azole, —C(=O)R, —C₁-C₆-alkyl(=O)R, and —C(=O)—NRR, wherein each R is independently hydrogen or C₁-C₆-alkyl, unsubstituted or substituted with one or more hydroxyl or halo;

R¹, R³, and R⁴ are hydrogen;

R² is hydroxyl-substituted-C₁-C₆-alkyl, halo-substituted-C₁-C₆-alkyl, amino-substituted-C₁-C₆-alkyl, —C(=O)—OH, —C(=O)R, —C₁-C₆-alkyl(=O)R, and —C(=O)—NRR, wherein each R is independently hydrogen or C₁-C₆-alkyl unsubstituted or substituted with one or more hydroxyl or halo; and pharmaceutically suitable salts thereof;

in combination with a pharmaceutically suitable carrier.

* * * * *